(12) United States Patent
Sugiura et al.

(10) Patent No.: US 11,186,508 B2
(45) Date of Patent: Nov. 30, 2021

(54) WATER TREATING AGENT AND KIT AND METHODS FOR PRODUCING AND USING

(71) Applicants: SEINEN INC., Gifu (JP); JAPAN ECOSYSTEM CO., LTD., Ichinomiya (JP)

(72) Inventors: Takehito Sugiura, Gifu (JP); Michiyo Sugiura, Gifu (JP)

(73) Assignees: SEINEN INC., Gifu (JP); JAPAN ECOSYSTEM CO., LTD., Ichinomiya (JP)

(*) Notice: Subject to any disclaimer, the term of this patent is extended or adjusted under 35 U.S.C. 154(b) by 0 days.

(21) Appl. No.: 17/285,981

(22) PCT Filed: Nov. 7, 2019

(86) PCT No.: PCT/JP2019/043697
§ 371 (c)(1),
(2) Date: Apr. 16, 2021

(87) PCT Pub. No.: WO2020/095999
PCT Pub. Date: May 14, 2020

(65) Prior Publication Data
US 2021/0317024 A1    Oct. 14, 2021

(30) Foreign Application Priority Data

Nov. 9, 2018   (JP) .............................. JP2018-211200

(51) Int. Cl.
*C02F 3/34* (2006.01)
*C02F 101/16* (2006.01)
*C02F 103/32* (2006.01)

(52) U.S. Cl.
CPC ........ *C02F 3/342* (2013.01); *C02F 2101/163* (2013.01); *C02F 2103/32* (2013.01)

(58) Field of Classification Search
None
See application file for complete search history.

(56) References Cited

U.S. PATENT DOCUMENTS

| 2010/0075390 | A1* | 3/2010 | Genin | ................... | B01J 23/007 |
| | | | | | 435/168 |
| 2014/0124454 | A1 | 5/2014 | Nichols et al. | | |
| 2018/0297864 | A1* | 10/2018 | Elsayed | ................. | C02F 1/288 |

FOREIGN PATENT DOCUMENTS

| JP | 2006-289338 A | 10/2006 |
| JP | 2013-184073 A | 9/2013 |

(Continued)

OTHER PUBLICATIONS

Communication dated Jul. 2, 2021, from the Intellectual property of India in application No. 202147020128.

(Continued)

*Primary Examiner* — Chester T Barry
(74) *Attorney, Agent, or Firm* — Sughrue Mion, PLLC

(57) ABSTRACT

An object of the invention is to provide a water treatment agent useful for reducing the MLSS and the like in a food factory effluent or the like and for reducing the total nitrogen of a water to be treated including nitrogen-containing compounds, a method for producing the water treatment agent, a method for treating water to be treated using the water treatment agent, and a kit for producing the water treatment agent. The water treatment agent of the invention is a water treatment agent that contains green rust and an enzymatic treatment agent containing a liver extract from a mammal (excluding a human being), a yeast lytic enzyme, lactate dehydrogenase, a glucose dehydrogenase, and water.

7 Claims, 7 Drawing Sheets

(56) References Cited

FOREIGN PATENT DOCUMENTS

| | | | |
|---|---|---|---|
| JP | 2013-184074 A | | 9/2013 |
| JP | 2013-184983 A | | 9/2013 |
| JP | 2013184073 A | * | 9/2013 |
| JP | 2013184074 A | * | 9/2013 |
| JP | 2016-502459 A | | 1/2016 |
| JP | 6347886 B1 | * | 6/2018 |
| JP | 6347886 B1 | | 6/2018 |
| JP | 2018-134597 A | | 8/2018 |
| KR | 101186814 B1 | | 9/2012 |
| WO | 2014189963 A1 | | 11/2014 |

OTHER PUBLICATIONS

International Search Report for PCT/JP2019/043697 dated Jan. 7, 2020 (PCT/ISA/210).

* cited by examiner

WATER TREATING AGENT AND KIT AND METHODS FOR PRODUCING AND USING

CROSS REFERENCE TO RELATED APPLICATIONS

This application is a National Stage of International Application No. PCT/JP2019/043697 dated Nov. 7, 2019, claiming priority based on Japanese Patent Application No. 2018-211200 dated Nov. 9, 2018

TECHNICAL FIELD

The present invention relates to a water treatment agent, a method for producing a water treatment agent, a method for treating water to be treated using a water treatment agent, and a kit for producing a water treatment agent.

BACKGROUND ART

Described in Patent Document 1 are a method for producing a green rust, the method including adjusting water in which a reduction catalyst body including 70 to 40 parts by mass of graphite and 20 to 50 parts by mass of at least one selected from the group consisting of iron and ferritic iron exists, with an acid to the range of pH 2 to 4, subsequently stirring the water to induce an oxidation-reduction reaction, adding 15 to 300 parts by mass of ferrous ion and/or a ferrous compound, checking whether the oxidation-reduction potential at the time of adjusting the pH to the range of 10.5±0.5 is in the range of −400 mV to −950 mV, terminating stirring and pH adjustment, and thereby obtaining green rust that is generated in the water (claim 1); and a method for treating water to be treated, the method including bringing a water to be treated, which includes at least one contaminant selected from the group consisting of aluminum, yttrium, zinc, copper, tin, chromium, silicon, iron, nickel, ions of these elements, and compounds of these elements, into contact with a green rust suspension (claim 6).

CITATION LIST

Patent Document

Patent Document 1: JP 6347886 B1

SUMMARY OF THE INVENTION

Problem to be Solved by the Invention

The green rust (magnetic carrier) described in Patent Document 1 was acknowledged to be effective for the reduction of the chemical oxygen demand (COD), the mixed liquor suspended solids (MLSS), total phosphorus (T-P), and the like in the water to be treated including nitrogen-containing compounds, such a food factory effluent; however, the total nitrogen (T-N) could not be sufficiently reduced.

Thus, an object of the invention is to provide a water treatment agent useful for reducing the MLSS and the like of a food factory effluent or the like and also for reducing the total nitrogen of a water to be treated including nitrogen-containing compounds, a method for producing the water treatment agent, a method for treating water to be treated using the water treatment agent, and a kit for producing the water treatment agent.

Means for Solving Problem

The inventors of the invention repeatedly conducted a thorough investigation in order to solve the above-described problems, and as a result, the inventors discovered that a water treatment agent containing green rust; and an enzymatic treatment agent containing a liver extract from a mammal (excluding a human being), a yeast lytic enzyme, lactate dehydrogenase, a glucose dehydrogenase, and water, is useful for reducing the total nitrogen in a water to be treated including nitrogen-containing compounds, such as a food factory effluent, thus completing the invention.

That is, the present inventors found that the above-described problems can be solved by the following configurations.

[1] A method for producing a water treatment agent, the method including obtaining a water treatment agent by mixing green rust; and an enzymatic treatment agent containing a liver extract from a mammal (excluding a human being), a yeast lytic enzyme, lactate dehydrogenase, a glucose dehydrogenase, and water.

[2] The method for producing a water treatment agent according to the above-described item [1], the method comprising:

a green rust generating step of adjusting water having a reduction catalyst body present therein, the reduction catalyst body including 40 parts by mass to 70 parts by mass of graphite and 20 parts by mass to 50 parts by mass of at least one selected from the group consisting of iron and ferritic iron, with an acid to the range of pH 2 to pH 5, stirring the water to induce an oxidation-reduction reaction, adding 15 parts by mass to 300 parts by mass of ferrous ion and/or a ferrous compound, checking whether the oxidation-reduction potential at the time of adjusting the pH to the range of 10.5±0.5 is −400 mV to −950 mV, terminating stirring and pH adjustment, and thereby obtaining green rust generated in the water; and a water treatment agent generating step of mixing the green rust with an enzymatic treatment agent, incubating the mixture for 3 days to 10 days at 5° C. to 35° C., and obtaining a water treatment agent generated in the mixed liquid, wherein the enzymatic treatment agent contains a liver extract from a mammal (excluding a human being), a yeast lytic enzyme, lactate dehydrogenase, a glucose dehydrogenase, and water.

[3] The method for producing a water treatment agent according to the above-described item [2], wherein the reduction catalyst body further includes 2 parts by mass to 10 parts by mass of at least one additive metal selected from the group consisting of aluminum, yttrium, zinc, copper, tin, chromium, and silicon, as metal and/or metal ferrite.

[4] The method for producing a water treatment agent according to the above-described item [2] or [3], wherein the reduction catalyst body includes 40 parts by mass to 70 parts by mass of graphite, 20 parts by mass to 50 parts by mass of at least one selected from the group consisting of iron and ferritic iron; and 2 parts by mass to 10 parts by mass of silicon ferrite.

[5] The method for producing a water treatment agent according to any one of the above-described items [2] to [4], wherein in the green rust generating step, the water having a reduction catalyst body present therein is adjusted with an acid to the range of pH 3.5 to pH 4.5, and the water is stirred to induce an oxidation-reduction reaction.

[6] The method for producing a water treatment agent according to any one of the above-described items [2] to [5], wherein in the green rust generating step, it is checked that the oxidation-reduction potential at the time of adjusting the pH to the range of 10.5±0.5 is in the range of −600 mV to −950 mV, and stirring and pH adjustment are terminated.

[7] The method for producing a water treatment agent according to the above-described item [1], wherein the method comprises:

a green rust generating step of adjusting water having a reduction catalyst body including 40 parts by mass to 70 parts by mass of graphite, 20 parts by mass to 50 parts by mass of ferritic iron, and 2 parts by mass to 10 parts by mass of silicon ferrite, with an acid to the range of pH 3.5 to pH 4.5, stirring the water to induce an oxidation-reduction reaction, adding 15 parts by mass to 300 parts by mass of ferrous ion and/or a ferrous compound, checking whether the oxidation-reduction potential at the time of adjusting the pH to the range of 10.5±0.5 is in the range of −600 mV to −950 mV, terminating stirring and pH adjustment, and thereby obtaining green rust generated in the water; and a water treatment agent generating step of mixing the green rust with an enzymatic treatment agent, incubating the mixture for 3 days to 10 days at 5° C. to 35° C., and obtaining a water treatment agent generated in the mixed liquid, and the enzymatic treatment agent contains a liver extract from a mammal (excluding a human being), a yeast lytic enzyme, lactate dehydrogenase, a glucose dehydrogenase, and water.

[8] The method for producing a water treatment agent according to any one of the above-described items [2] to [7], wherein the reduction catalyst body is a powder or a lump material.

[9] The method for producing a water treatment agent according to any one of the above-described items [2] to [8], wherein in the green rust generating step, the green rust is obtained as a green rust suspension.

[10] The method for producing a water treatment agent according to any one of the above-described items [2] to [9], wherein in the water treatment agent generating step, the water treatment agent is obtained as a water treatment agent suspension.

[11] A method for treating water to be treated, the method comprising bringing a water to be treated including nitrogen-containing compounds, into contact with a water treatment agent suspension obtained by the method according to the above-described item [10].

[12] The method for treating water to be treated according to the above-described item [11], wherein the nitrogen compounds include nitrate nitrogen.

[13] The method for treating water to be treated according to the above-described item [10] or [11], wherein the water to be treated is an effluent from a food factory.

[14] A method for treating water to be treated by cyclically using a sediment, the method comprising:

Step 1 of adding a water treatment agent suspension obtained by the method according to the above-described item [10] to the water to be treated according to the above-described items [11] to [13], which is raw water in a treatment tank, adjusting the pH, and then stirring the mixture;

Step 2 of separating a sediment and treated water from the treated water obtained in Step 1;

Step 3 of removing sludge from the separated sediment;

Step 4 of adding a portion or the entirety of the sediment from which sludge has been removed, into the water to be treated according to any one of the above-described items [5] to [7], which is raw water, adding the water treatment agent suspension obtained by the method according to the above-described item [4] thereto, adjusting the pH, and then stirring the mixture;

Step 5 of separating a sediment and treated water from the treated water obtained in Step 4; and Step 6 of repeating Step 3 and Step 4 once or several times after Step 5, and then obtaining a sediment and the total amount of treated water.

[15] A water treatment agent comprising:

green rust; and an enzymatic treatment agent containing a liver extract from a mammal (excluding a human being), a yeast lytic enzyme, lactate dehydrogenase, a glucose dehydrogenase, and water.

[16] A kit for producing a water treatment agent suspension, the kit comprising:

a first container accommodating a green rust suspension;

a second container accommodating an enzymatic treatment agent containing a liver extract from a mammal (excluding a human being), a yeast lytic enzyme, lactate dehydrogenase, a glucose dehydrogenase, and water; and an instruction manual describing a method for producing a water treatment agent suspension from the green rust suspension and the enzymatic treatment agent.

Effect of the Invention

According to the invention, a water treatment agent that is useful for reducing the MLSS and the like of a food factory effluent or the like and also for reducing the total nitrogen in a water to be treated including nitrogen-containing compounds, a method for producing the water treatment agent, a method for treating water to be treated using the water treatment agent, and a kit for producing the water treatment agent, can be provided.

MODE(S) FOR CARRYING OUT THE INVENTION

Figure 1:
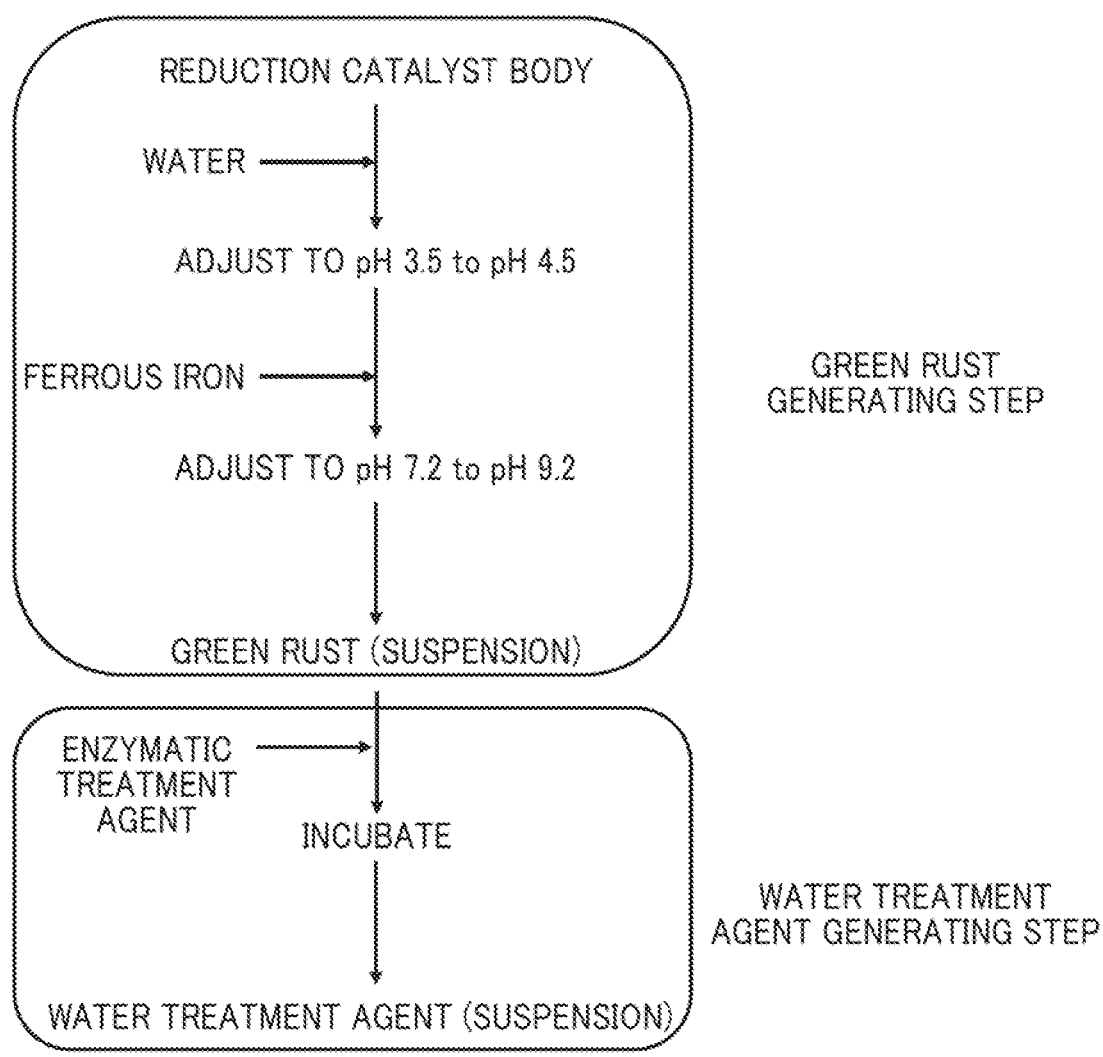
FIG. 1 is a flow diagram illustrating a method for producing a water treatment agent according to the invention.

According to the invention, a range expressed using the term "to" is defined to include both ends of the term "to". For example, a range expressed as "A to B" includes "A" and "B".

Hereinafter, the acronyms used in the present specification represent the following abbreviations, and the measurement conditions are as follows.

The total iron equivalent concentration in the green rust suspension was measured by an ICP quantitative analysis.

ORP stands for Oxidation-Reduction Potential (unit: mV). On the basis of Ag/AgCl electrodes, in the present specification, a liquid to be measured is adjusted to pH 10.5 with caustic soda, and measurement is made.

COD stands for Chemical Oxide Demand (unit: mg/L). The chemical oxide demand is a value obtained by oxidizing oxidizable substances in a sample water using an oxidizing agent under certain conditions, determining the amount of oxygen required for oxidation from the amount of the oxidizing agent used at that time, and converting the amount of oxygen. The oxidizable substances include various organic substances and inorganic substances such as nitrites and sulfides; however, main oxidizable substances are organic substances. The COD is measured by an acidic high-temperature permanganate method ($COD_{Mn}$).

TOC stands for Total Organic Carbon (unit: mg/L). The organic matter state carbon included in a sample water is oxidized into carbon dioxide. Then, the TOC is determined by measuring the amount of the carbon dioxide. The TOC is measured by a combustion oxidation method.

DO stands for Dissolved Oxygen (unit: mg/L). This means the concentration of oxygen dissolved in water and is expressed by how many mg of oxygen is included in 1 L of water. The DO is measured by the Winkler method.

SV stands for activated sludge precipitation rate (Sludge Volume; unit: %). Unless particularly stated otherwise, SV30 is represented by a volume ratio of a portion settling from a suspension for 30 minutes. The precipitation rate of a sediment is represented by a volume ratio of the solid content settling from a suspension.

MLSS stands for the quantity of suspended solids in a sludge mixed liquid (Mixed Liquor Suspended Solids; unit: mg/L) inside an aerator (aeration tank) for an activated sludge treatment.

[Water Treatment Agent]

The water treatment agent according to the invention is a water treatment agent containing green rust and an enzymatic treatment agent. The green rust is not particularly limited; however, it is preferably green rust that is produced in the above-described green rust generating step.

<Green Rust>

Green rust is a transparent pale blue-colored or transparent pale green-colored substance in which ferrous hydroxide and ferric hydroxide are stratified. Specific examples of green rust are described in JP 6347886 B1, JP 5170461 B2, and the like.

<Enzymatic Treatment Agent>

The above-described enzymatic treatment agent is as will be described below.

The content of green rust in the water treatment agent is not particularly limited; however, for the reason that the effect of the invention is superior, the content of green rust is preferably 0.3% to 3.0% by mass, and more preferably 0.5% to 2.5% by mass.

Furthermore, the content of the enzymatic treatment agent in the water treatment agent is not particularly limited; however, for the reason that the effect of the invention is superior, the content of the enzymatic treatment agent is preferably 0.0002% to 0.003% by mass, and more preferably 0.0005% to 0.002% by mass.

Furthermore, for the reason that the effect of the invention is superior, the proportion of the content of the enzymatic treatment agent with respect to the content of green rust (content of enzymatic treatment agent/content of green rust) in the water treatment agent is preferably 0.001% to 10% by mass, more preferably 0.01% to 1% by mass, and even more preferably 0.05% to 0.5% by mass.

Incidentally, it is speculated that a suitable range of the content of green rust varies depending on the type of nitrogen (for example, organic state nitrogen, nitrate nitrogen, or ammonia nitrogen) in the water to be treated.

For example, in the case of ammonia nitrogen, when a green rust suspension is added to an ammonia-containing aqueous solution, in ammonia ($NH_3$), hydrogen atoms are gravitated toward nitrogen atoms. Regarding the electronegativity, the value for nitrogen (N) is 3.0, and in water ($H_2O$), since hydrogen atoms are gravitated toward oxygen atoms, the electronegativity is 3.5. Since nitrogen (N) 3.0<oxygen (O) 3.5, it is speculated that a shared pair of electrons of a water molecule exist unevenly toward the side of an atom with higher electronegativity ($OH^-$) therein, and due to uneven distribution of the electric charge in the molecule, the hydrogen atoms of ammonia are gravitated toward the oxygen atom having strong electronegativity (since $OH^-$ is a rare gas, it is outside the definition) to form water ($H_2O$), while the nitrogen atoms are released as nitrogen ($N_2$) to the atmosphere, so that harmlessness is achieved.

Furthermore, it is speculated that nitrate nitrogen carries out, when a green rust suspension is added thereto, a proton release reaction: $OH+OH^- \rightarrow -O^- + H_2O$ and decomposes oxyanion ions.

Furthermore, organic state nitrogen is speculated to have the same function as ammonia, and it is thought that the incorporated content value is larger than that of ammonia.

The range of the content is considered such that the smallest value corresponds to the case of ammonia, while the largest value corresponds to the case of nitrate nitrogen.

[Method for Producing Water Treatment Agent]

The method for producing a water treatment agent according to the invention is a method for producing a water treatment agent, the method including mixing green rust with an enzymatic treatment agent and thereby obtaining the above-described water treatment agent of the invention.

Incidentally, the details of the green rust and the enzymatic treatment agent will be described below.

For the reason that the effect of the invention is superior, it is preferable that the method for producing a water treatment agent according to the invention comprises a green rust generating step and a water treatment agent generating step (FIG. 1).

<Green Rust Generating Step>

As a suitable embodiment of the green rust generating step, a green rust generating step of adjusting water in which a reduction catalyst body including 40 parts by mass to 70 parts by mass of graphite and 20 parts by mass to 50 parts by mass of at least one selected from the group consisting of iron and ferritic iron, with an acid to the range of pH 2 to pH 5, stirring the mixture to induce an oxidation reduction reaction, adding 15 parts by mass to 300 parts of ferrous ion and/or a ferrous compound, checking whether the oxidation-reduction potential at the time of adjusting the pH to the range of 10.5±0.5 is in the range of −400 mV to −950 mV, terminating stirring and pH adjustment, and obtaining green rust generated in the water, may be mentioned. A specific example of such a green rust generating step is described in, for example, JP 6347886 B1.

With regard to the green rust generating step, it is preferable to obtain the green rust as a green rust suspension.

(Reduction Catalyst Body)

The reduction catalyst body includes 40 parts by mass to 70 parts by mass of graphite and 20 parts by mass to 50 parts by mass of at least one selected from the group consisting of iron and ferritic iron.

The reduction catalyst body may further include 2 parts by mass to 10 parts by mass of at least one additive metal selected from the group consisting of aluminum, yttrium, zinc, copper, tin, chromium, and silicon, as metal and/or metal ferrite.

It is preferable that the reduction catalyst body includes 40 parts by mass to 70 parts by mass of graphite, 20 parts by mass to 50 parts by mass of at least one selected from the group consisting of ferrite and ferritic iron, and 2 parts by mass to 10 parts by mass of silicon ferrite, and it is more preferable that the reduction catalyst body includes 40 parts by mass to 70 parts by mass of graphite, 20 parts by mass to 50 parts by mass of ferritic iron, and 2 parts by mass to 10 parts by mass of silicon ferrite.

The reduction catalyst body may be a powder and/or a lump material; however, it is preferable that the reduction catalyst body is a powder.

Graphite is not particularly limited and may be either natural graphite or artificial graphite; however, natural graphite is preferred. Furthermore, since a graphite having a larger surface area exhibits increased reactivity, graphite in a powder form is preferred.

The ferritic iron is not particularly limited; however, for example, as described in paragraph [0026] of JP 6347886 B1, ferritic iron extracted from a sediment generated in a settling tank during an effluent treatment using green rust (suspension) can be utilized. Furthermore, a commercially available product of ferritic iron may be purchased. Since a ferritic iron having a larger surface area exhibits increased reactivity, ferritic iron in a powder form is preferred.

Silicon ferrite is not particularly limited; however, for example, as described in paragraph [0026] of JP 6347886 B1, silicon ferrite extracted from a sediment generated in a settling tank during an effluent treatment using green rust (suspension) can be utilized. Furthermore, a commercially available product of silicon ferrite may be purchased. Since a silicon ferrite having a larger surface area exhibits increased reactivity, silicon ferrite in a powder form is preferred.

(Oxidation-Reduction Reaction)

In the green rust generating step, the oxidation-reduction reaction is carried out by adjusting the water having a reduction catalyst body present therein, with an acid to the range of pH 2 to pH 5, and stirring the mixture to induce an oxidation-reduction reaction; however, it is preferable to adjust the pH to the range of pH 3.5 to pH 4.5.

(Oxidation-Reduction Potential)

In the green rust generating step, the oxidation-reduction potential at the time of adjusting the pH to the range of 10.5±0.5 is in the range of −400 mV to −950 mV; however, it is preferable that the oxidation-reduction potential is in the range of −600 mV to −950 mV.

<Water Treatment Agent Generating Step>

The water treatment agent generating step is a step of mixing the green rust (may be a suspension) generated in the green rust generating step with an enzymatic treatment agent, and incubating the mixture for 3 days to 10 days at 5° C. to 35° C. to obtain a water treatment agent generated in the mixed liquid.

The water treatment agent may be obtained as a suspension. Incidentally, the water treatment agent obtained as a suspension is also simply referred to as "water treatment agent".

(Enzymatic Treatment Agent)

The enzymatic treatment agent is the "enzymatic treatment agent" described in JP 5963241 B2.

The enzymatic treatment agent is a water-based composition containing a liver extract from a mammal (excluding a human being), a yeast lytic enzyme, lactate dehydrogenase, a glucose dehydrogenase, and water.

The enzymatic treatment agent can be produced by mixing a liver extract from a mammal (excluding a human being), a yeast lytic enzyme, lactate dehydrogenase, and a glucose dehydrogenase to prepare a mixed liquid (A), preparing a mixed liquid (B) by using the mixed liquid (A) as it is or after removing solid matter, and preparing a mixed liquid (C) by using the mixed liquid (B) as it is or after mixing with water.

As a more specific production method for the enzymatic treatment agent, the production method described in Example 1 of JP 5963241 B2 may be mentioned.

Raw materials (a) to (d) are prepared.

(a) Pig's liver extract (CT-3000, manufactured by Intec USA, LLC)

(b) Yeast lytic enzyme (manufactured by Kanto Chemical Co., Inc.; 5000 U/g)

(c) Lactate dehydrogenase (pig's heart) (EC 1.1.1.27; 2000 U/mL)

(d) Glucose dehydrogenase (EC 1.1.1.47; 250 U/mg)

Production is carried out according to procedures (1) to (8).

(1) The pig's liver extract is filtered through a filter (polymer separation membrane, pore size 1.2 to 20 μm).

(2) To 2000 g of the filtrate of the pig's liver extract, 200 g of the yeast lytic enzyme, 15 mg of the lactate dehydrogenase, and 10 mg of the glucose dehydrogenase are added, and the mixture is stirred and mixed.

(3) This mixed liquid is left to stand for 10 days while being refrigerated at 0° C. to 5° C.

(4) Subsequently, the mixed liquid is further left to stand for 3 days while being kept warm at 38° C. to 40° C.

(5) This mixed liquid is filtered through a filter (polymer separation membrane, pore size 0.45 to 1.2 μm).

(6) 500 g of the filtered mixed liquid is added to 2000 g of purified water, the total amount is made up to 20000 g with purified water, and the mixture is stirred and mixed.

(7) This mixed liquid is left to stand for 3 days while being maintained at normal temperature (5° C. to 35° C.)

(8) After the standing, the mixed liquid is stored at normal temperature while avoiding direct sunlight.

[Method for treating water to be treated]

Figure 2:
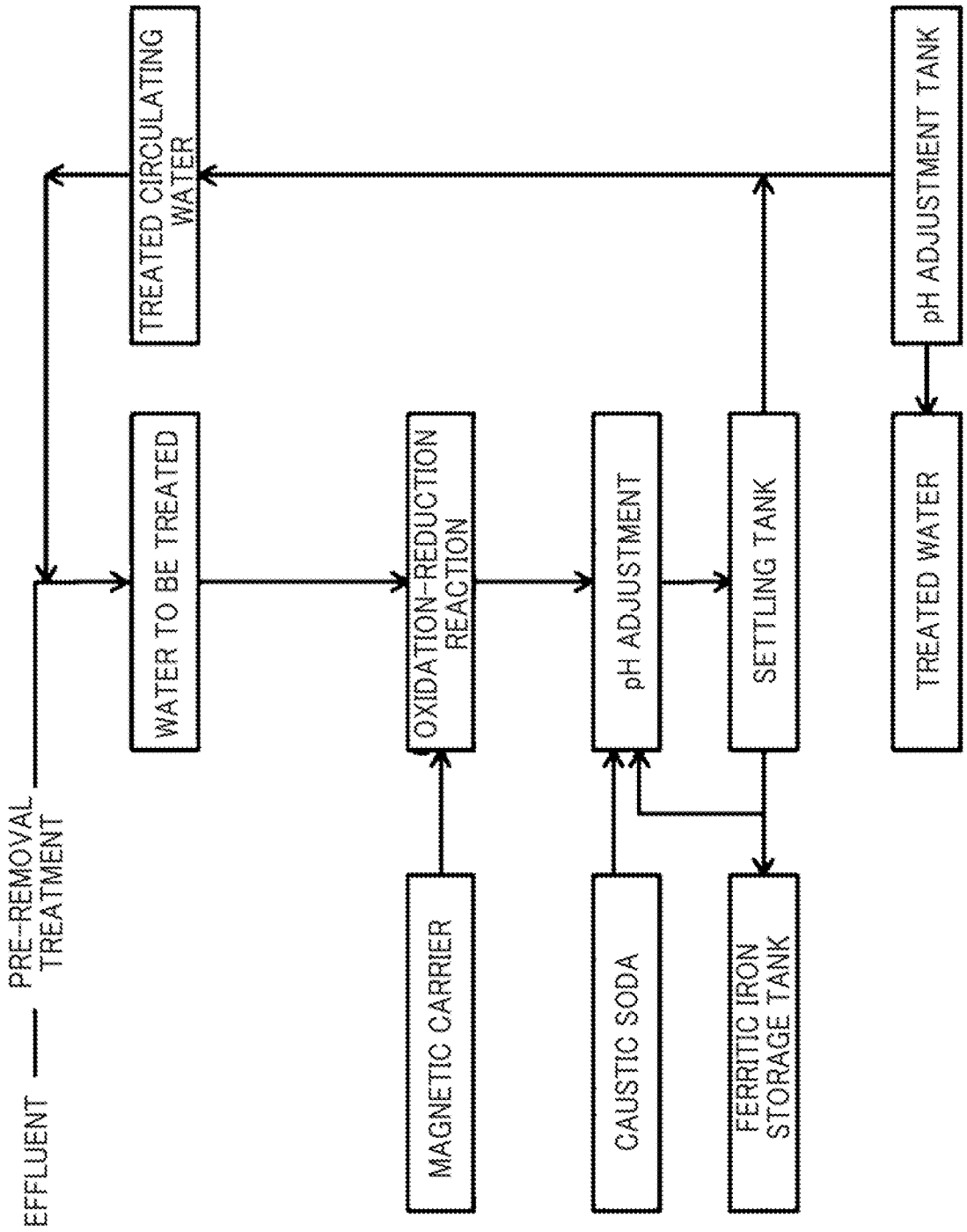
FIG. 2 is a flow diagram illustrating a method for treating water to be treated using a water treatment agent according to the invention.

A method for treating water to be treated according to the invention involves bringing a water to be treated including nitrogen-containing compounds into contact with the water treatment agent of the invention (FIG. 2).

Regarding mixing with water to be treated, it is preferable that the water treatment agent of the invention is mixed with the water to be treated in the early stage of water treatment, and for example, the water treatment agent is preferably mixed with the water to be treated in an aeration tank; however, in a case where water is circulated, the mixing may take place at any site.

The pH of the water treatment agent of the invention at the time of bringing the water treatment agent of the invention into contact with water to be treated, is not particularly limited; however, the pH is preferably in the range of pH 7.2±0.5 to pH 9.2±0.5, and more preferably in the range of pH 7.2±0.2 to pH 9.2±0.2.

It is preferable that the nitrogen compounds include nitrate nitrogen. The water treatment agent of the invention is useful for the reduction of the total amount of nitrogen (T-N), which also includes nitrate nitrogen.

Furthermore, it is preferable that the water to be treated is an effluent from a food factory (food factory effluent). The water treatment agent of the invention is useful for the reduction of the total amount of nitrogen (T-N) of a water to be treated having a large total amount of nitrogen (T-N), such as a food factory effluent.

In the method for treating water to be treated according to the invention, it is preferable to cyclically use a sediment.

The method for treating water to be treated by cyclically using a sediment comprises Step 1 of adding the water treatment agent of the invention to water to be treated, adjusting the pH, and stirring the mixture; Step 2 of separating a sediment and treated water from the treated water obtained in Step 1; Step 3 of removing sludge from the separated sediment; Step 4 of adding a portion or the entirety of the sediment, from which sludge has been removed, into the water to be treated, adding the water treatment agent according to the invention, adjusting the pH, and stirring the mixture; Step 5 of separating a sediment and treated water from the treated water obtained in Step 4; and Step 6 of repeating Step 3 and Step 4 once or several times after Step 5, and then obtaining a sediment and the total amount of treated water.

[Kit]

A kit according to the invention comprises a first container accommodating a green rust suspension; a second container accommodating an enzymatic treatment agent; and a manual describing the above-described method for producing a water treatment agent of the invention from a green rust suspension and an enzymatic treatment agent. The kit is a kit for producing the above-described water treatment agent according to the invention.

The green rust is not particularly limited; however, the green rust is preferably a green rust that is produced by the above-described green rust generating step.

The enzymatic treatment agent is as described above.

By using a kit that accommodates a green rust suspension and an enzymatic treatment agent respectively in separate containers, the mixing ratio of the green rust suspension and the enzymatic treatment agent can be freely set by a user, and customization adapted to the field of use is enabled.

EXAMPLES

Hereinafter, the invention will be more specifically described by way of Examples; however, the scope of the invention is not intended to be limited to the Examples described below.

[Production Example 1] Production of Green Rust (Suspension)

10 L of water was introduced into a water tank, a material (reduction catalyst body) obtained by mixing and stirring 600 g of graphite and 400 g of ferritic iron ($Fe_3O_4$) was put into a filter fabric on the inner side of a long tube-shaped punched stainless steel sheet and was immovably immersed in the water. While the water was stirred, the pH was adjusted to the range of pH 3.5 to pH 4.5 using dilute sulfuric acid.

After the water was stirred for 40 hours, 1200 g of ferrous sulfate ($FeSO_4 \cdot 7H_2O$) was added thereto while the water was stirred. The oxidation-reduction potential (ORP) upon addition was lowered to 400 mV or less.

The changes in pH and ORP during this process are shown in the following table.

TABLE 1

| Measured values of pH and ORP | | | | | |
|---|---|---|---|---|---|
| pH | | | ORP | | |
| Start point | End point | Reduction coefficient [1/h] | Start point [mV] | End point [mV] | Reduction coefficient [mV/h] |
| 3.5 | 6.53 | 0.1262 | 314.6 | 72.3 | 10.095 |

After further stirring the water for 40 hours, an aqueous solution of sodium hydroxide (48% (w/v)) was added thereto to adjust the pH to 10.5 while the water was stirred, a reduction test was performed, it was checked that the oxidation-reduction potential (ORP) was in the range of −700 mV to −800 mV, and then stirring and pH adjustment were terminated. The generation of green rust was confirmed by checking whether the color was transparent pale blue color or transparent pale green color. The green rust suspension in the tank was filtered through a filtering filter using a transfer pump and then was stored in a storage container.

[Production Example 2] Production of Silicon Ferrite

<Materials and Method>

500 mL of a green rust suspension (suspension produced in Production Example 1; total iron concentration 32000 mg/L, pH 10.5, ORP −720 mV) was introduced into a 500-mL beaker, 2.8 mL of an aqueous solution of sodium hydroxide (48% (w/v)) was added thereto while stirring was performed, and thus the pH of the green rust suspension was adjusted to pH 10.5. 5 g of a silicon dioxide ($SiO_2$) powder was gently added to the green rust suspension whose pH had been adjusted, while stirring was performed.

At every 2 hours from the time point of adding the silicon dioxide powder to a time point after 14 hours, the pH, oxidation-reduction potential (ORP), dissolved oxygen content (DO), and hue of the green rust suspension were monitored while stirring was performed. The results of monitoring are shown in the following table. Meanwhile, the silicon content (Si) was determined by performing a quantitative analysis by an inductively coupled plasma (ICP) method at the time of adding silicon dioxide.

TABLE 2

| Green rust suspension | | | | | |
|---|---|---|---|---|---|
| | | pH | ORP [mV] | DO [mg/L] | Si [mg/L] | Hue |
| Time after initiation of | 0 | 10.5 | −771 | 0.1 | 4300 | Dark green |
| | 2 | 10.5 | −718 | 0.2 | — | Dark green |

TABLE 2-continued

Green rust suspension

|  |  | pH | ORP [mV] | DO [mg/L] | Si [mg/L] | Hue |
|---|---|---|---|---|---|---|
| monitoring | 4 | 10.3 | −694 | 9.4 | — | Dark green |
|  | 6 | 9.7 | −516 | <20 | — | Green |
|  | 8 | 9.1 | −392 | <20 | — | Pale brown |
|  | 10 | 8.6 | −284 | <20 | — | Pale brown |
|  | 12 | 8.1 | −217 | <20 | — | Black brown |
|  | 14 | 7.8 | −124 | 7.8 | — | Black brown |

Stirring was stopped after 14 hours from the time of adding a silicon dioxide powder to the green rust suspension.

At every 2 hours from the time point of stopping stirring to a time point after 6 hours, the pH, oxidation-reduction potential (ORP), dissolved oxygen content (DO), hue, and settling rate of the supernatant of the green rust suspension were monitored. The results of monitoring are shown in the following table. Meanwhile, the silicon content (Si) in the supernatant separated liquid was determined by performing a quantitative analysis by an inductively coupled plasma (ICP) method after 6 hours from the time point of termination of stirring.

TABLE 3

Supernatant of green rust suspension

|  |  | pH | ORP [mV] | DO [mg/L] | Si [mg/L] | Hue | Settling rate [%] |
|---|---|---|---|---|---|---|---|
| Time after stop stirring | 2 | 8.2 | −241 | 6.4 | — | Black | 60 |
|  | 4 | 8.3 | −254 | 3.1 | — | Black | 40 |
|  | 6 | 8.5 | −266 | 0.7 | ≤0.01 | Black | 20 |

It was found that the oxygen of silicon dioxide was detached by the green rust suspension, and the dissolved oxygen content (DO) was increased; however, settling started after a lapse of 12 hours, the dissolved oxygen content (DO) of the supernatant was decreased by precipitation of a green rust sediment, and the amount of silicon in the supernatant separated water was decreased to 0.01 mg/L or less.

It was found that as the oxyanion of silicon dioxide was released, oxidation of green rust proceeded, and ferrite generation proceeded.

A neodymium magnet (surface magnetic flux density (T) 0.42, adsorptive force (N) 25.48, diameter 10 mm) was put into the settled sediment, and the settled sediment was all adsorbed.

The silicon ferrite suspension obtained by the above-described method was vacuum filtered, the sediment was heated for 4 hours at 90° C. using a drying furnace, subsequently the sediment was taken out from the furnace and left to naturally cool, and thus silicon ferrite (powder) was obtained.

[Example 1] Production of Water Treatment Agent

For each (A, B, C, and D) of materials (reduction catalyst bodies) obtained by mixing and stirring a graphite powder, a ferritic iron powder, and a silicon ferrite powder (produced in Production Example 2) at the proportions shown in the following table, the reduction catalyst body was put into a filter fabric on the inner side of a long tube-shaped punched stainless steel sheet and was immovably immersed in the water. While the water was stirred, the pH was adjusted to the range of pH 3.5 to pH 4.5 using dilute sulfuric acid. The total content of the graphite powder, the ferritic iron powder, and the silicon ferrite powder in 1 L of water is 100 g.

After the water was stirred for one hour, 120 g of ferrous sulfate ($FeSO_4 \cdot 7H_2O$) was added to 1 L of water while the water was further stirred. While the aqueous solution was stirred, the aqueous solution was sampled after 1 hour, after 2 hours, and after 3 hours from the addition, the pH of the aqueous solution was adjusted to pH 10.5±0.5 using an aqueous solution of sodium hydroxide (48% (w/v)), and then the oxidation-reduction potential (ORP) was measured. The compositions of the respective reduction catalyst bodies and the measured values of ORP of the respective examples are shown in the following table. As such, green rust suspensions were produced.

TABLE 4

Compositions of reduction catalyst bodies and measured values of ORP

|  |  | A | B | C | D |
|---|---|---|---|---|---|
| Graphite [mass %] |  | 55 | 55 | 55 | 55 |
| Ferritic iron [mass %] |  | 35 | 37.5 | 40 | 45 |
| Silicon ferrite [mass %] |  | 10 | 7.5 | 5 | 0 |
| ORP [mV] | After 1 hour | −421 | −414 | −424 | −417 |
|  | After 2 hours | −542 | −576 | −605 | −489 |
|  | After 3 hours | −631 | −708 | −758 | −584 |

Regarding the oxidation-reduction potential (ORP), a mixing ratio of 55% by mass of carbon, 40% by mass of ferritic iron, 5% of ferrite silicate, and 40% of ferritic iron with a reaction time of 3 hours gave the best results.

For a material (reduction catalyst body) obtained by mixing and stirring 55% by mass of a graphite powder, 40% by mass of a ferritic iron powder, and 5% by mass of a silicon ferritic powder (powder produced in Production Example 2), the reduction catalyst body was put into a filter fabric on the inner side of a long tube-shaped punched stainless steel sheet and was immovably immersed in water. While the water was stirred, the pH was adjusted to the range of pH 3.5 to pH 4.5 using dilute sulfuric acid.

After the water was stirred for one hour, 60 g (E), 90 g (F), 120 g (G), 150 g (H), or 180 g (I) of ferrous sulfate ($FeSO_4 \cdot 7H_2O$) was added to 1 L of water while the water was further stirred. While the aqueous solution was stirred, the aqueous solution was sampled after 1 hour, after 2 hours, and after 3 hours from the addition, the pH of the aqueous solution was adjusted to pH 10.5±0.1 using an aqueous solution of sodium hydroxide (48% (w/v)), and then the oxidation-reduction potential (ORP) was measured. The amount of addition of ferrous sulfate and the measured values of ORP of the respective examples are shown in the following table.

TABLE 5

Amount of addition of ferrous sulfate and measured values of ORP

| Amount of ferrous sulfate amount of addition [g/l] |  | E 60 | F 90 | G 120 | H 150 | I 180 |
|---|---|---|---|---|---|---|
| ORP [mV] | After 1 hour | −426 | −429 | −424 | −405 | −401 |
|  | After 2 hours | −588 | −582 | −605 | −592 | −577 |
|  | After 3 hours | −767 | −761 | −758 | −714 | −687 |
|  | After 4 hours | −824 | −815 | −807 | −786 | −744 |

There was observed a tendency that as the amount of addition of ferrous sulfate was larger, the decrease in ORP was slow, and as the amount of addition was smaller, the decrease in ORP was fast.

A green rust suspension produced by the above-described C and an enzymatic treatment agent produced according to the production method described in Example 1 of JP 5963241 B2 and having the pH adjusted to pH 7.2±0.2 were mixed at a volume ratio of 90:10 and stirred. After stirring, the mixture was transferred into another container and incubated for 5 days at 22° C. in a constant temperature storehouse, and thus a water treatment agent was produced in the state of suspension. The content of green rust in the water treatment agent was approximately 1.0% by mass, and the content of the enzymatic treatment agent in the water treatment agent was approximately 0.001% by mass.

The pH was adjusted to 10.5 by adding an aqueous solution of sodium hydroxide (48% (w/v)), and the oxidation-reduction potential (ORP) was measured, which was found to be −703 mV.

Incidentally, the enzymatic treatment agent (enzymatic treatment agent Z) was produced by the materials and method described below.
<Materials>
(1) Pig's liver extract (CT-3000, manufactured by Intec USA, LLC)
(2) Yeast lytic enzyme (manufactured by Kanto Chemical Co., Inc.; 5000 U/g)
(3) Lactate dehydrogenase (pig's heart) (EC 1.1.1.27; 2000 U/mL)
(4) Glucose dehydrogenase (EC 1.1.1.47; 250 U/mg)
<Method>
(1) The pig's liver extract was filtered through a filter (polymer separation membrane, pore size 1.2 to 20 μm).
(2) To 2000 g of the filtrate of the pig's liver extract, 200 g of the yeast lytic enzyme, 15 mg of the lactate dehydrogenase, and 10 mg of the glucose dehydrogenase were added, and the mixture was stirred and mixed.
(3) This mixed liquid was left to stand for 10 days while being refrigerated at 0° C. to 5° C.
(4) Subsequently, the mixed liquid was further left to stand for 3 days while being kept warm at 38° C. to 40° C.
(5) This mixed liquid was filtered through a filter (polymer separation membrane, pore size 0.45 to 1.2 μm).
(6) 500 g of the filtered mixed liquid was added to 2000 g of purified water, the total amount was made up to 20000 g with purified water, and the mixture was stirred and mixed.
(7) This mixed liquid was left to stand for 3 days while being maintained at normal temperature (5° C. to 35° C.)
(8) After the standing, the mixed liquid was stored at normal temperature while avoiding direct sunlight.

The component names and mixing amounts of the enzymatic treatment agent (enzymatic treatment agent Z) thus produced are shown in the following table.

TABLE 6

| Enzymatic treatment agent Z | | | |
|---|---|---|---|
| | Component name | Mixing amount | |
| Mixed liquid (A1) | Pig's liver extract (filtrate) | 2000 | g |
| | Yeast lytic enzyme | 200 | g |
| | Lactate dehydrogenase | 15 | mg |
| | Glucose dehydrogenase | 10 | mg |
| | Total amount | 2200 | g |

TABLE 6-continued

| Enzymatic treatment agent Z | | | |
|---|---|---|---|
| | Component name | Mixing amount | |
| Mixed liquid (B1) | Mixed liquid (A1) | 500 | g |
| | Purified water | 19500 | g |
| | Total amount | 20000 | g |

[Comparative Example 1] Production of Green Rust (Suspension)

For a material (reduction catalyst body) obtained by mixing and stirring 55% by mass of a graphite powder, 40% by mass of a ferritic iron powder, and 5% by mass of a silicon ferrite powder (powder produced in Production Example 2), the reduction catalyst body was put into a filter fabric on the inner side of a long tube-shaped punched stainless steel sheet and was immovably immersed in water. While the water was stirred, the pH was adjusted to the range of pH 3.5 to pH 4.5 using dilute sulfuric acid.

After stirring for one hour, 120 g of ferrous sulfate ($FeSO_4 \cdot 7H_2O$) was added to 1 L of water while the water was further stirred.

Furthermore, after stirring for 40 hours, an aqueous solution of sodium hydroxide (48% (w/v)) was added thereto to adjust the pH to 10.5 while the water was stirred, a reduction test was performed, it was confirmed that the oxidation-reduction potential (ORP) was in the range of −700 mV to −800 mV, and then stirring and pH adjustment were terminated. The generation of green rust was confirmed by checking whether the color was transparent pale blue color or transparent pale green color. The green rust suspension in the tank was filtered through a filtering filter using a transfer pump and then was stored in a storage container.

[Reference Examples 2 to 4] Reaction of Green Rust Suspension Toward Activated Sludge The pH of the green rust suspension produced in Production Example 1 and stored was adjusted from pH 4.2 to pH 7.2 (Reference Example 2) or pH 9.2 (Reference Example 3) using an aqueous solution of sodium hydroxide (48% (w/v)).

An aeration tank sludge mixed liquid from a wastewater treatment plant of a food processing factory was collected and used as an activated sludge sample. The properties of the activated sludge sample thus collected, and the properties of supernatant separated water were as follows. Meanwhile, the MLSS conformed to the sewage test method, Chapter 3, Section 6, and the MLVSS conformed to the sewage test method, Chapter 3, Section 7.

TABLE 7

| Properties of activated sludge | | | | |
|---|---|---|---|---|
| pH | MLSS [mg/L] | MLVSS [mg/L] | SV30 [%] | SV90 [%] |
| 7.6 | 5100 | 4600 | 99 | 95 |

TABLE 8

| Properties of supernatant separated water | | | | | |
|---|---|---|---|---|---|
| Iron [mg/L] | Phosphorus [mg/L] | TOC [mg/L] | COD [mg/L] | BOD [mg/L] | T-N [mg/L] |
| 1.4 | 0.8 | 24.2 | 8 | 3.2 | 12.6 |

A stirring device and an aerator were installed in a beaker having a volume of 2000 mL, and three sets of test water tanks in which aeration and stirring could be performed were prepared.

Reference Example 2

2000 mL of the activated sludge sample (as described above) was introduced into the above-described test water tank, and the activated sludge sample was stirred for one hour while being aerated the sample at an aeration rate of 0.5 L/min.

While the active sludge sample was aerated and stirred, the green rust suspension (as described above) that had been adjusted to pH 7.2 was added thereto in an amount of 500 mg per 1 L of the activated sludge sample, and aeration and stirring were further continued. The pH, MLSS, SV30, SV90, iron, phosphorus, T-N, TOC, and COD of the sample solution in the test water tank were monitored, and thereby the measured values after 24 hours, after 48 hours, and after 72 hours from the addition of the green rust suspension were recorded. The monitoring results are shown in the following table.

Reference Example 3

2000 mL of the activated sludge sample (as described above) was introduced into the test water tank, and the activated sludge sample was stirred for one hour while being aerated at an aeration rate of 0.5 L/min.

While the activated sludge sample was aerated and stirred, the green rust suspension (as described above), which had been adjusted to pH 9.2, was added thereto in an amount of 500 mg per 1 L of the activated sludge sample, and aeration and stirring were further continued. The pH, MLSS, SV30, SV90, iron, phosphorus, T-N, TOC, and COD of the sample solution in the test water tank were monitored, and thereby the measured values after 24 hours, after 48 hours, and after 72 hours from the addition of the green rust suspension were recorded. The monitoring results are shown in the following table.

Reference Example 4

2000 mL of the activated sludge sample (as described above) was introduced into the test water tank, and the activated sludge sample was stirred for one hour while being aerated at an aeration rate of 0.5 L/min.

While the activated sludge sample was aerated and stirred, water was added thereto in an amount of 500 mg per 1 L of the activated sludge sample, and aeration and stirring were further continued. The pH, MLSS, SV30, SV90, iron, phosphorus, T-N, TOC, and COD of the sample solution in the test water tank were monitored, and thereby the measured values after 24 hours, after 48 hours, and after 72 hours from the addition of the green rust suspension were recorded. The monitoring results are shown in the following table.

TABLE 9

| | Measured values after addition of green rust suspension | | | | |
|---|---|---|---|---|---|
| | | | Reference Example | | |
| | | | 2 | 3 | 4 |
| 0 hours | pH | | 7.6 | 7.7 | 7.6 |
| 24 hours | pH | | 7.6 | 7.6 | 7.5 |
| | MLSS | [mg/L] | 5000 | 5000 | 5000 |
| | SV30 | [%] | 98 | 96 | 99 |
| | SV90 | [%] | 93 | 90 | 95 |
| | Iron | [mg/L] | 2.1 | 1.9 | 1.4 |
| | Phosphorus | [mg/L] | 0.6 | 0.6 | 0.8 |
| | T-N | [mg/L] | 12.2 | 12.7 | 14.6 |
| | TOC | [mg/L] | 21.7 | 20.4 | 23.7 |
| | COD | [mg/L] | 2.6 | 2.4 | 2.7 |
| 48 hours | pH | | 7.6 | 7.6 | 7.5 |
| | MLSS | [mg/L] | 4700 | 4700 | 5000 |
| | SV30 | [%] | 94 | 87 | 99 |
| | SV90 | [%] | 84 | 78 | 96 |
| | Iron | [mg/L] | 1.8 | 1.7 | 1.5 |
| | Phosphorus | [mg/L] | 0.7 | 0.4 | 1.3 |
| | T-N | [mg/L] | 14.9 | 15.1 | 16.2 |
| | TOC | [mg/L] | 20.4 | 19.2 | 22.1 |
| | COD | [mg/L] | 2.5 | 2.6 | 2.8 |
| 72 hours | pH | | 7.5 | 7.5 | 7.3 |
| | MLSS | [mg/L] | 4600 | 4600 | 4900 |
| | SV30 | [%] | 87 | 86 | 99 |
| | SV90 | [%] | 74 | 74 | 97 |
| | Iron | [mg/L] | 1.5 | 1.2 | 1.5 |
| | Phosphorus | [mg/L] | 0.3 | 0.2 | 1.2 |
| | T-N | [mg/L] | 15.7 | 15.9 | 18.7 |
| | TOC | [mg/L] | 21.2 | 19.4 | 22.7 |
| | COD | [mg/L] | 2.2 | 2.3 | 2.9 |

The variations over time in the SV30 and SV90 of Reference Examples 2 to 4 are shown in the following table.

TABLE 10

| | Variations in SV30 and SV90 | | | | | |
|---|---|---|---|---|---|---|
| | | | Reference Example | | | |
| | | | 2 | 3 | 4 | Determination |
| 0 hours | SV30 | [%] | 99 | 99 | 99 | — |
| | SV90 | [%] | 95 | 95 | 95 | |
| 24 hours | SV30 | [%] | 94 | 87 | 99 | Δ |
| | SV90 | [%] | 84 | 74 | 96 | |
| 48 hours | SV30 | [%] | 94 | 87 | 99 | ○ |
| | SV90 | [%] | 84 | 74 | 96 | |
| 72 hours | SV30 | [%] | 87 | 86 | 99 | ○ |
| | SV90 | [%] | 74 | 74 | 97 | |
| Determination | | | ○ | ○ | — | |

The symbol "Δ" of the determination indicates that the settling rate improved slightly, and the symbol "○" indicates that the improvement in the settling rate was very clear.

The pH of the green rust suspension did not affect the SV30 and the SV90.

The settling properties improved after a lapse of 48 hours from the time point of addition of the green rust suspension.

The increases or decreases over time in the amount of activated sludge of Reference Examples 2 to 4 are shown in the following table.

TABLE 11

Increase or decrease in activated sludge (MLSS)

| | | | Reference Example | | | |
|---|---|---|---|---|---|---|
| | | | 2 | 3 | 4 | Determination |
| 0 hours | MLSS | [mg/L] | 5000 | 5000 | 5000 | — |
| 24 hours | MLSS | [mg/L] | 5000 | 5000 | 5000 | × |
| 48 hours | MLSS | [mg/L] | 4700 | 4700 | 5000 | ○ |
| 72 hours | MLSS | [mg/L] | 4600 | 4600 | 4900 | ○ |

The symbol "X" of the determination indicates that there was no reduction in the quantity of the activated sludge (MLSS), the symbol "Δ" indicates that there was a slight reduction in quantity, and the symbol "○" indicates that there was a conspicuous improvement.

The pH of the green rust suspension did not affect the MLSS.

The quantity of the MLSS decreased after a lapse of 48 hours from the time point of addition of the green rust suspension, and the state of quantity reduction continued thereafter.

The variation in the soluble iron content (Fe) of Reference Examples 2 to 4 are shown in the following table.

TABLE 12

Variation in soluble iron content (Fe)

| | | | Reference Example | | | |
|---|---|---|---|---|---|---|
| | | | 2 | 3 | 4 | Determination |
| 0 hours | Iron | [mg/L] | 1.4 | 1.4 | 1.4 | — |
| 24 hours | Iron | [mg/L] | 2.1 | 1.8 | 1.4 | Δ |
| 48 hours | Iron | [mg/L] | 2.1 | 1.8 | 1.5 | Δ |
| 72 hours | Iron | [mg/L] | 1.5 | 1.2 | 1.5 | ○ |

The symbol "Δ" of the determination indicates that the dissolved amount slightly increased, and the symbol "○" indicates that the dissolved amount decreased.

The dissolved amount of iron temporarily increased immediately after the addition of the green rust suspension; however, as the time passed, the green rust suspension was converted to magnetite (magnetic carrier), and the soluble iron content decreased.

The variation in the phosphorus content (P) of Reference Examples 2 to 4 are shown in the following table.

TABLE 13

Variation in phosphorus content (P)

| | | | Reference Example | | | |
|---|---|---|---|---|---|---|
| | | | 2 | 3 | 4 | Determination |
| 0 hours | Phosphorus | [mg/L] | 0.8 | 0.8 | 0.8 | — |
| 24 hours | Phosphorus | [mg/L] | 0.6 | 0.6 | 0.8 | ○ |
| 48 hours | Phosphorus | [mg/L] | 0.7 | 0.4 | 1.3 | ○ |
| 72 hours | Phosphorus | [mg/L] | 0.3 | 0.2 | 1.2 | ⊙ |

The symbol "X" of the determination indicates that the phosphorus content exceeded the water quality regulation value, the symbol "Δ" indicates that the phosphorus content increased slightly, the symbol "○" decreased, and the symbol "⊙" indicates that the phosphorus content decreased to a large extent in Reference Examples 1 and 2.

The variation in the total nitrogen (T-N) of Reference Examples 2 to 4 are shown in the following table.

TABLE 14

Variation in total nitrogen (T-N) content

| | | | Reference Example | | | |
|---|---|---|---|---|---|---|
| | | | 2 | 3 | 4 | Determination |
| 0 hours | T-N | [mg/L] | 12.6 | 12.6 | 12.6 | — |
| 24 hours | T-N | [mg/L] | 12.2 | 12.7 | 14.6 | Δ |
| 48 hours | T-N | [mg/L] | 14.9 | 15.1 | 16.2 | × |
| 72 hours | T-N | [mg/L] | 15.7 | 15.9 | 18.7 | × |

The symbol "X" of the determination indicates that the T-N value exceeds the value of 0 hours, and the symbol "Δ" indicates that the T-N value increased slightly.

In all of Reference Examples 2 to 4, the total nitrogen (T-N) increased.

Since the increase in the total nitrogen (T-N) tended to increase over time, it was considered that such a tendency was due to a nitrification reaction.

The variations in the TOC and COD of Reference Examples 2 to 4 are shown in the following table.

TABLE 15

Variations in TOC and COD

| | | | Reference Example | | | |
|---|---|---|---|---|---|---|
| | | | 2 | 3 | 4 | Determination |
| 0 hours | TOC | [mg/L] | 24.2 | 24.2 | 24.2 | — |
| | COD | [mg/L] | 8 | 8 | 8 | |
| 24 hours | TOC | [mg/L] | 21.2 | 20.4 | 23.7 | ○ |
| | COD | [mg/L] | 2.6 | 2.4 | 2.7 | |
| 48 hours | TOC | [mg/L] | 20.4 | 19.2 | 22.1 | ○ |
| | COD | [mg/L] | 2.5 | 2.6 | 2.8 | |
| 72 hours | TOC | [mg/L] | 21.2 | 19.4 | 22.7 | ○ |
| | COD | [mg/L] | 2.2 | 2.3 | 2.9 | |

The symbol "○" of the determination indicates that the TOC and COD decreased to values less than the value of 0 hours.

Example 2/Comparative Example 5/Comparative Example 2

The aeration tank sludge mixed liquids from a wastewater treatment plant of a food processing factory, which were the same as the activated sludges used in Reference Examples 2 to 4 as described above, were collected and used as activated sludge samples.

A stirring device and an aerator were installed in a beaker having a volume of 2000 mL, and two sets of test water tanks in which aeration and stirring could be performed were prepared.

Example 2

An aqueous solution of sodium hydroxide (48% (w/v)) was added to the water treatment agent produced in Example 1, and the pH was adjusted to 7.2±0.2.

2000 mL of the activated sludge sample (as described above) was introduced into the above-described test water tank, and the activated sludge sample was stirred for one hour while being aerated at an aeration rate of 0.5 L/min.

While the activated sludge sample was aerated and stirred, the pH-adjusted water treatment agent was added thereto in an amount of 500 mg per 1 L of the activated sludge sample, and aeration and stirring were further continued. The total amount of nitrogen (T-N) of the sample solution in the test water tank was monitored, and thereby the measured values were recorded every single day from a time point immediately after the addition of the water treatment agent (day 0) to a time point after 7 days. The monitoring results are shown in the following table.

Comparative Example 5

An aqueous solution of sodium hydroxide (48% (w/v)) was added to the green rust suspension produced in Comparative Example 1, and the pH was adjusted to 7.2±0.2.

2000 mL of the activated sludge sample (as described above) was introduced into the test water tank, and the activated sludge sample was stirred for one hour while being aerated at an aeration rate of 0.5 L/min.

While the active sludge sample was aerated and stirred, the pH-adjusted green rust suspension was added thereto in an amount of 500 mg per 1 L of the activated sludge sample, and aeration and stirring were further continued. The total amount of nitrogen (T-N) of the sample solution in the test water tank was monitored, and thereby the measured values were recorded every single day from a time point immediately after the addition of the water treatment agent (day 0) to a time point after 7 days. The monitoring results are shown in the following table.

TABLE 16

| Variation in total nitrogen (T-N) | | | |
|---|---|---|---|
| | | Example 2 | Comparative Example 5 |
| T-N [mg/L] | After 0 days | 12.8 | 12.8 |
| | After 1 day | 10.6 | 12.8 |
| | After 2 days | 8.4 | 15.1 |
| | After 3 days | 8.6 | 16.4 |
| | After 4 days | 8.8 | 17.2 |
| | After 5 days | 8.6 | 17.7 |
| | After 6 days | 8.9 | 17.4 |
| | After 7 days | 8.4 | 16.8 |
| Determination | | ◯ | X |

The symbol "X" of the determination indicates that the total nitrogen (T-N) was not reduced to a value less than the value of 0 days, and the symbol "◯" indicates that the total nitrogen (T-N) was reduced to a value less than the value of 0 days.

In Example 2, it was successful in reducing the total nitrogen (T-N). It is thought to be because a nitrification reaction in the water to be treated could be avoided.

Furthermore, the MLSS was evaluated according to [Example 3/Comparative Example 6] that will be described below, and the MLSS was more decreased in Example 2 than in Comparative Example 5.

Comparative Example 2

2000 mL of the activated sludge sample (as described above) was introduced into the above-described test water tank, and the activated sludge sample was stirred for one hour while being aerated at an aeration rate of 0.5 L/min.

While the activated sludge sample was aerated and stirred, the above-mentioned enzymatic treatment agent used in Example 1 was added thereto in an amount equivalent to the content of the enzymatic treatment agent in the water treatment agent used in Example 2, and aeration and stirring were further continued. The total amount of nitrogen (T-N) of the sample solution in the test water tank was monitored, and thereby the measured values were recorded every single day from a time point immediately after the addition of the water treatment agent (day 0) to a time point after 7 days. The monitoring results are shown in the following table.

As a result, the total nitrogen decreased; however, the decrement was not as large as that of Example 2.

Furthermore, the MLSS was evaluated according to [Example 3/Comparative Example 6] that will be described below, and the MLSS of Comparative Example 2 was not significantly changed.

<Measurement of Particle Size Distribution>

The particle size distributions (on a volume basis) of the activated sludge sample on the $3^{rd}$ day of experiment of Example 2 and the activated sludge sample on the $3^{rd}$ day of experiment of Comparative Example 5 were measured.

(Measurement Method and Measurement Conditions)
Measuring equipment: Optical table MT3300 (Low-WET)
Measuring sample: Activated sludge sample on 3rd day of experiment of Example 2
  Activated sludge sample on 3rd day of experiment of Comparative Example 5
Measurement upper limit (μm): 2000
Measurement lower limit (μm): 0.021
Solvent name: Water
Solvent refractive index: 1.333
Distribution display: Volume
Residual ratio (%): 0.00
Particle refractive index: 1.60
DV value: 0.2484
Transmittance (TR): 0.915

Figure 3:
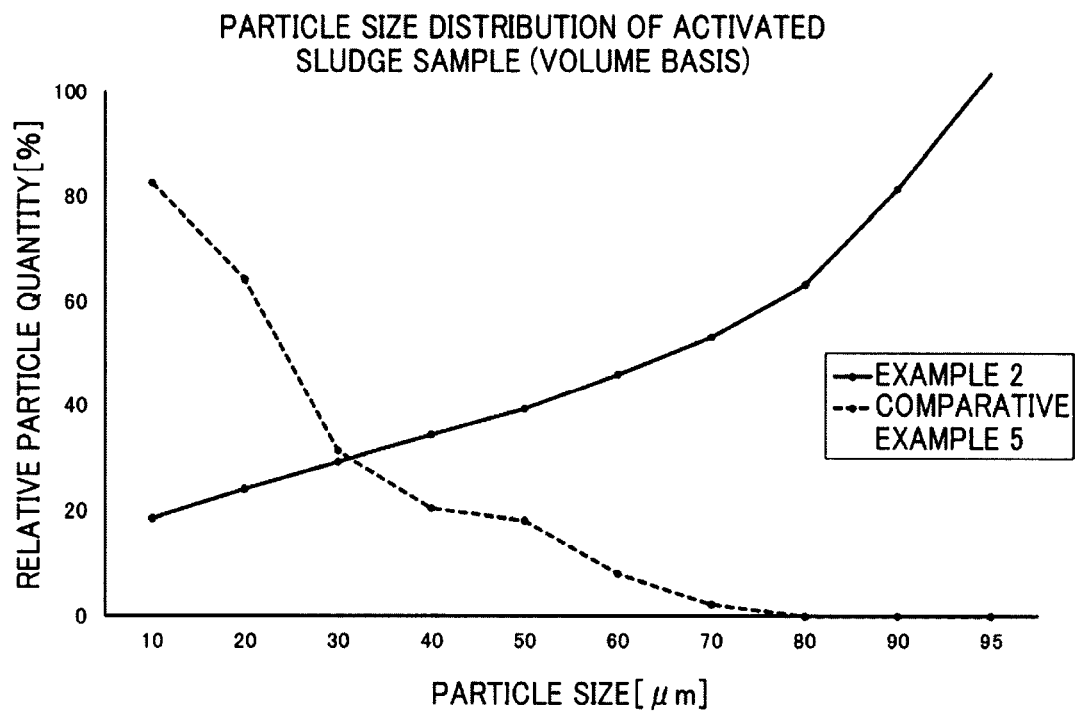
FIG. 3 is a graph showing the particle size distribution (on a volume basis) of activated sludge samples of Example 2 and Comparative Example 5.

The particle size distributions (on a volume basis) of the activated sludge samples obtained by measurement are shown in the following table and graph (FIG. 3).

TABLE 17

| Particle size distribution of activated sludge sample | | |
|---|---|---|
| | Relative particle quantity [%] | |
| Particle size [μm] | Example 2 | Comparative Example 5 |
| 10 | 18.45 | 82.65 |
| 20 | 24.17 | 64.24 |
| 30 | 29.32 | 31.23 |
| 40 | 34.37 | 20.45 |
| 50 | 39.38 | 18.17 |
| 60 | 45.89 | 7.92 |
| 70 | 53.14 | 2.21 |
| 80 | 63.12 | 0 |
| 90 | 81.45 | 0 |
| 95 | 103.4 | 0 |

The particle size that gave the largest relative particle quantity in the particle size distribution of the activated sludge sample of Example 2 was 95 μm; however, the particle size that gave the largest relative particle quantity in the particle size distribution of the activated sludge sample of Comparative Example 5 was 10 μm.

From a comparison between Example 2, Comparative Example 5, and Comparative Example 2, it was verified that the water treatment agent of Example 2 that used green rust and a specific enzymatic treatment agent in combination was superior in both the effect of reducing the MSLL and the effect of reducing the total amount of nitrogen, as compared to Comparative Example 5 that used green rust only and Comparative Example 2 that used a specific enzymatic treatment agent only.

When the water treatment agent of the invention was added to an activated sludge sample, the electrons of a shared pair of electrons of a water molecule retained by the green rust (magnetic carrier) in the water treatment agent exist unevenly toward the side of an atom with higher electronegativity ($OH^-$), and due to uneven distribution of the electric charge in the molecule, colloidal particles (activated sludge microorganisms) are electrochemically supplied with electrons, promote activity in the growth process, and perform adsorption and assimilation. The iron (Fe (+2)⇔Fe (+3)) contained in the magnetic carrier completes valence conversion, and iron is converted to ferritic iron that retains magnetism by interatomic oscillation action in time and space, becomes turbid into an activated sludge turbid liquid, and makes the electron transport out of microbial cells active (magnetite) to be mixed into sludge. Thereby, electricity flows through ferrite particles, symbiotic metabolism is enhanced, the growth of electron-producing microorganisms is promoted, the crowding ability of the microorganisms is enhanced to a large extent, the sludge settling rate of the activated sludge on the magnetic carrier and the settling speed are improved, and the thereby the water quality values such as colorant, phosphorus, and nitrogen can also be reduced.

With regard to the water treatment agent according to the invention, a biological species that transfers electrons to ferritic iron as an electron acceptor by using organic waste as energy, without using any external power source, is an iron-reducing bacterium, and an iron-reducing bacterium can transfer electrons that have been produced inside the cells to the outside through the cell membrane, such that by means of this function, the iron-reducing bacterium converts waste organic matter into energy (electron donor) without using the high energy of conventional effluent treatment. Thus, the water treatment agent can achieve energy saving and enhance the capacity of conventional activated sludge treatment.

Example 3/Comparative Example 6

A treatment was carried out using a food factor effluent as water to be treated.

The water quality of the water to be treated (influent raw water) of the food factory effluent and the goals for water quality of treated water are shown in the following table.

TABLE 18

Water quality of raw water of food factory effluent and goals for water quality of treated water

| Item | | Water quality of raw water | Goals for water quality of treated water |
|---|---|---|---|
| pH | | 4.2 to 6.4 | 5.8 to 7.5 |
| BOD | [mg/L] | 1800 to 2100 | 20 |
| COD | [mg/L] | 2000 to 2200 | 20 |
| SS | [mg/L] | 50 to 200 | 50 |
| T-N | [mg/L] | 80 to 120 | 10 |
| T-P | [mg/L] | 30 to 40 | 1 |
| N-hexane | [mg/L] | 20 to 35 | 5 |

The amount of raw water influent to a food effluent treatment facility and the facility capacity are shown in the following table.

TABLE 19

Amount of raw water and facility capacity

| Name | Quantity | Unit |
|---|---|---|
| Amount of influent raw water | 250 to 280 | $m^3$/day |
| Flow rate adjusting tank | 260 | $m^3$ |
| Anaerobic tank | 320 | $m^3$ |
| Aeration tank | 720 | $m^3$ |

Example 3

300 mg/L of the water treatment agent produced in Example 1 was added to an anaerobic tank of the food factory effluent treatment facility using a metering pump.

Regarding the food factory effluent, since there are variations in the manufactured product, when the load is large, the water quality of the treated water may exceed standard values.

Figure 4:
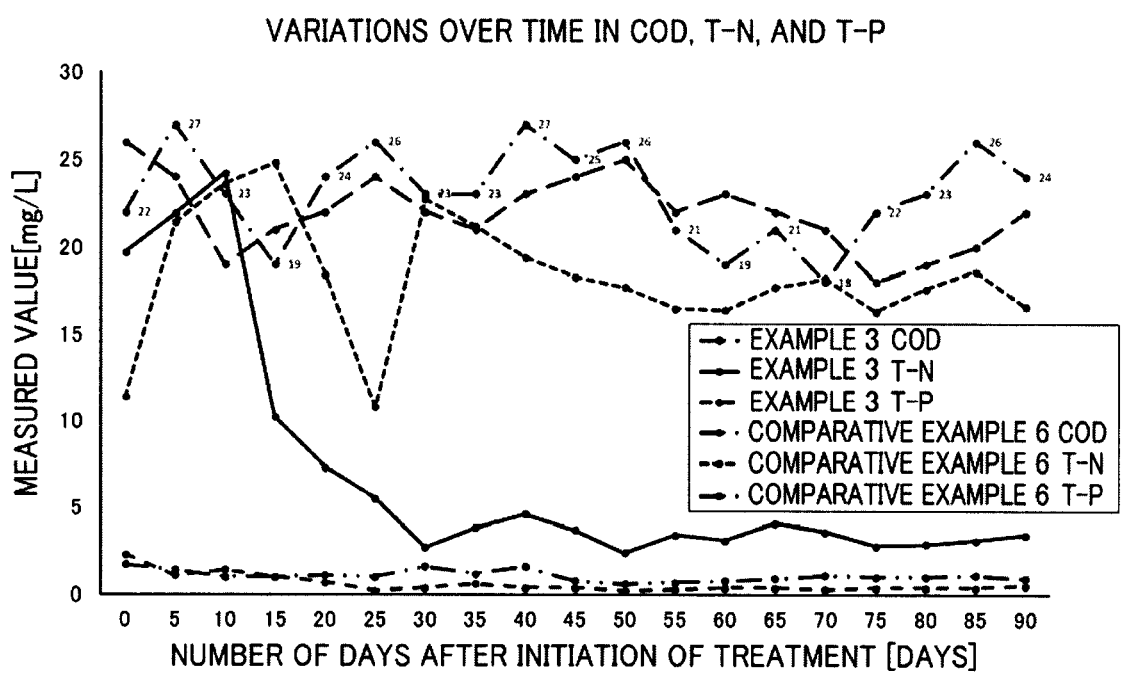
FIG. 4 is a graph showing variations over time in the chemical oxygen demand (COD), the total nitrogen (T-N), and the total phosphorus (T-P) of Example 3 and Comparative Example 6.

After the initiation of treatment, the chemical oxygen demand (COD), the total nitrogen (T-N), and the total phosphorus (T-P) of the treated water were measured. The measured values of COD, T-N, and T-P recorded every five days from the treatment initiation day (day 0) to a time point after 90 days are shown in the following table. Furthermore, a graph is shown in FIG. 4.

Comparative Example 6

A food factory effluent was treated using a food factory effluent treatment facility. A water treatment agent was not added.

After the initiation of treatment, the chemical oxygen demand (COD), the total nitrogen (T-N), and the total phosphorus (T-P) of the treated water were measured. The measured values of COD, T-N, and T-P recorded every five days from the treatment initiation day (day 0) to a time point after 90 days are shown in the following table. Furthermore, a graph is shown in FIG. 4.

TABLE 20

Variations over time in COD, T-N, and T-P

| | | Example 3 | | | Comparative Example 6 | | |
|---|---|---|---|---|---|---|---|
| | | COD [mg/L] | T-N [mg/L] | T-P [mg/L] | COD [mg/L] | T-N [mg/L] | T-P [mg/L] |
| Number of days after initiation of treatment | 0 | 26 | 19.7 | 2.3 | 22 | 11.4 | 1.7 |
| | 5 | 24 | 21.9 | 1.1 | 27 | 21.4 | 1.4 |
| | 10 | 19 | 24.2 | 1.4 | 23 | 23.6 | 1 |
| | 15 | 21 | 10.2 | 1 | 19 | 24.8 | 1 |
| | 20 | 22 | 7.3 | 0.7 | 24 | 18.4 | 1.1 |
| | 25 | 24 | 5.5 | 0.2 | 26 | 10.8 | 1 |
| | 30 | 22 | 2.7 | 0.4 | 23 | 22.7 | 1.6 |
| | 35 | 21 | 3.8 | 0.6 | 23 | 21.2 | 1.2 |
| | 40 | 23 | 4.6 | 0.4 | 27 | 19.4 | 1.6 |
| | 45 | 24 | 3.7 | 0.4 | 25 | 18.3 | 0.8 |
| | 50 | 25 | 2.4 | 0.2 | 26 | 17.7 | 0.6 |
| | 55 | 22 | 3.4 | 0.3 | 21 | 16.5 | 0.7 |
| | 60 | 23 | 3.1 | 0.4 | 19 | 16.4 | 0.8 |
| | 65 | 22 | 4.1 | 0.4 | 21 | 17.7 | 0.9 |
| | 70 | 21 | 3.6 | 0.3 | 18 | 18.2 | 1.1 |
| | 75 | 18 | 2.8 | 0.4 | 22 | 16.3 | 1 |
| | 80 | 19 | 2.9 | 0.4 | 23 | 17.6 | 1 |
| | 85 | 20 | 3.1 | 0.4 | 26 | 18.6 | 1.1 |
| | 90 | 22 | 3.4 | 0.5 | 24 | 16.6 | 0.9 |
| Average value | | 22 | 6.96 | 0.62 | 23.1 | 18.29 | 1.08 |

In Example 3 where a water treatment agent was used, the T-N was reduced, and the goal for T-N reduction was also achieved. On the other hand, in Comparative Example 6 where a water treatment agent was not used, the T-N was not reduced, and the goal for T-N reduction was also not achieved.

<Quantity of Suspended Solids>

Figure 5:
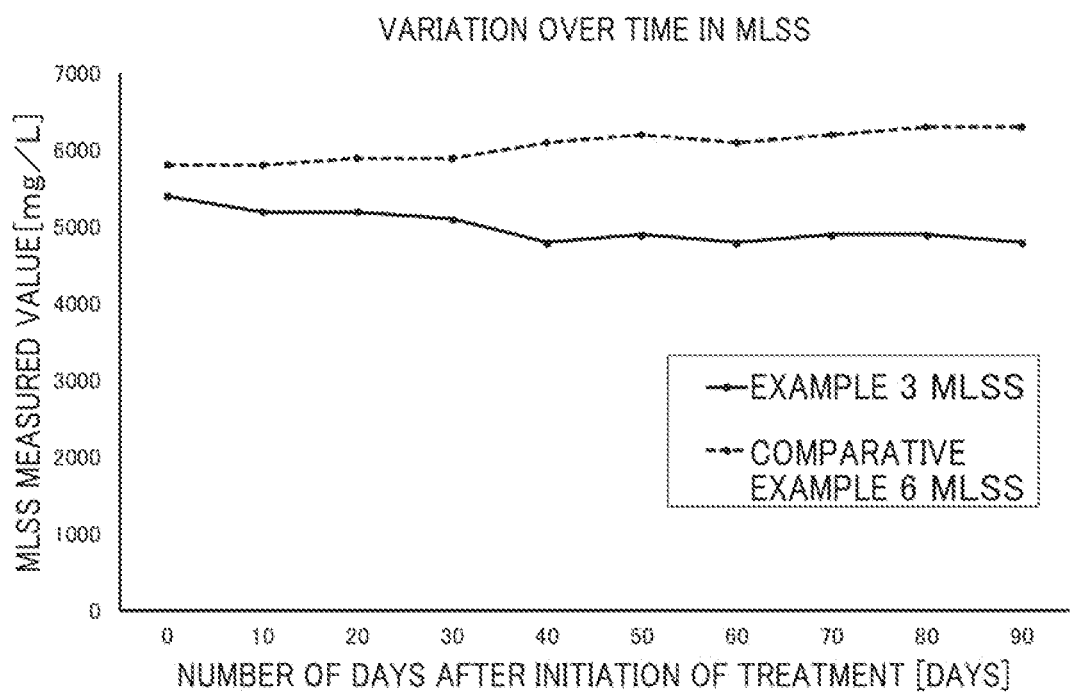
FIG. 5 is a graph showing the mixed liquor suspended solids (MLSS) of Example 3 and Comparative Example 6.

In Example 3 and Comparative Example 6, after the initiation of treatment, the quantity of suspended solids (MLSS) of the treated water was measured and recorded every ten days from the treatment initiation day (day 0) to a time point after 90 days. The measured values are shown in the following table. Furthermore, a graph is shown in FIG. 5.

TABLE 21

Variation over time in MLSS

|  |  | Example 3 MLSS [mg/L] | Comparative Example 6 MLSS [mg/L] |
|---|---|---|---|
| Number of days after initiation of treatment | 0 | 5400 | 5800 |
|  | 10 | 5200 | 5800 |
|  | 20 | 5200 | 5900 |
|  | 30 | 5100 | 5900 |
|  | 40 | 4800 | 6100 |
|  | 50 | 4900 | 6200 |
|  | 60 | 4800 | 6100 |
|  | 70 | 4900 | 6200 |
|  | 80 | 4900 | 6300 |
|  | 90 | 4800 | 6300 |
| Average value |  | 5000 | 6060 |

The mixed liquor suspended solids (MLSS) decreased mildly in Example 3; however, a tendency of increase was recognized in Comparative Example 6. It is considered that in Example 6, the sludge is adsorbed and assimilated on the surface of fine particles of the magnetic carrier in the water treatment agent.

[Additional Experiments]

In order to check the effect of the enzymatic treatment agent, more detailed additional experiments were carried out, and therefore, the experiments will be described below.

For the activated sludge sample, an aeration tank sludge mixed liquid from a wastewater treatment plant of a food processing factor was collected and used. The properties of the activated sludge sample were as follows.

(Properties of Activated Sludge)

TABLE 22

| pH | MLSS (mg/l) | MLVSS (mg/l) | SV30 (%) | SV90 (%) |
|---|---|---|---|---|
| 7.8 | 5300 | 4500 | 99 | 97 |

MLSS: Sewage testing method Chapter 3 Section 6
MLVSS: Sewage testing method Chapter 3 Section 7
(Supernatant Separated Water)

TABLE 23

| Iron (mg/l) | Phosphorus (mg/l) | TOC (mg/l) | COD (mg/l) | BOD (mg/l) | T-N (mg/l) |
|---|---|---|---|---|---|
| 2.1 | 0.8 | 28.7 | 14 | 5.6 | 16.4 |

The following comparison experiment was carried out using the present sample.

(Experimental Method for Comparing Optimum Amount of Addition of Enzymatic Treatment Agent)

Three containers for performing aeration and stirring at an aeration rate of 0.5 L/min, in which 2000 ml of the above-described activated sludge sample was introduced into a 2000-ml container, and an aerator was installed therein to perform stirring of the sample, were prepared, each of the containers was stirred for one hour, subsequently the enzymatic treatment agent was diluted with purified in a ten-fold amount, an arbitrary amount (0 mg/l, 100 mg/l, or 200 mg/l) of the dilution was added to the container, the water quality and properties of the activated sludge were traced and measured for 24 to 72 hours, and the optimum amount of addition was determined.

(Experiment for Adding Enzymatic Treatment Agent)

TABLE 24

| Time (h) | Measurement item | Blank | 100 mg/l | 200 mg/l |
|---|---|---|---|---|
| Start | pH | 7.8 | 7.8 | 7.8 |
| 24 | pH | 7.7 | 7.8 | 7.7 |
|  | MLSS (mg/l) | 5300 | 5300 | 5100 |
|  | SV30 (%) | 99 | 99 | 99 |
|  | SV90 (%) | 97 | 97 | 97 |
|  | Phosphorus (mg/l) | 0.8 | 0.8 | 0.8 |
|  | T-N (mg/l) | 17.6 | 16.4 | 16.1 |
|  | TOC (mg/l) | 25.4 | 22.7 | 21.5 |
|  | COD (mg/l) | 8.5 | 7.7 | 6.7 |
| 48 | pH | 7.6 | 7.4 | 7.5 |
|  | MLSS (mg/l) | 5200 | 5100 | 5100 |
|  | SV30 (%) | 99 | 98 | 97 |
|  | SV90 (5) | 96 | 92 | 90 |
|  | Phosphorus (mg/l) | 0.7 | 0.7 | 0.7 |
|  | T-N (mg/l) | 19.4 | 13.3 | 12.8 |
|  | TOC (mg/l) | 24.6 | 22.4 | 20.2 |
|  | COD (mg/l) | 4.4 | 4.3 | 4.3 |
| 72 | pH | 7.3 | 7.5 | 7.5 |
|  | MLSS (mg/l) | 5100 | 500 | 4900 |
|  | SV30 (%) | 98 | 98 | 98 |
|  | SV90 (%) | 97 | 96 | 97 |
|  | Phosphorus (mg/l) | 0.7 | 0.6 | 0.7 |
|  | T-N (mg/l) | 24.6 | 14.7 | 11.3 |
|  | TOC (mg/l) | 23.7 | 22.6 | 18.9 |
|  | COD (mg/l) | 6.4 | 5.8 | 4.7 |

(Experiment Results) (Sludge Settling Rate)

TABLE 25

| Amount of addition | Start (%) | 24 hours (%) | 48 hours (%) | 72 hours (%) | Determination |
|---|---|---|---|---|---|
| Blank | 99$_{(30)}$/ 97$_{(90)}$ | 99$_{(30)}$/ 97$_{(90)}$ | 99$_{(30)}$/ 96$_{(90)}$ | 98$_{(30)}$/ 97$_{(90)}$ | — |
| 100 mg/l | 99$_{(30)}$/ 97$_{(90)}$ | 99$_{(30)}$/ 97$_{(90)}$ | 98$_{(30)}$/ 92$_{(90)}$ | 98$_{(30)}$/ 96$_{(90)}$ | X |
| 200 mg/l | 99$_{(30)}$/ 97$_{(90)}$ | 99$_{(30)}$/ 97$_{(90)}$ | 97$_{(30)}$/ 90$_{(90)}$ | 98$_{(30)}$/ 97$_{(90)}$ | X |

The symbol X of the determination indicates that the settling rate was not improved, the symbol Δ indicates that the settling rate was slightly improved, and the symbol ○ indicates that the improvement in the settling rate was conspicuous.

The results were such that there was no variation in the sludge settling properties depending on the amount of addition of the enzymatic treatment agent, and there was also no variation in the reaction time.

(Experiment Results)
Suspended sludge concentration (MLSS) unit: mg/l

TABLE 26

| Amount of addition | Start | 24 hours | 48 hours | 72 hours | Determination |
|---|---|---|---|---|---|
| Blank | 5300 | 5300 | 5200 | 5100 | — |
| 100 mg/l | 5300 | 5300 | 5100 | 5000 | Δ |
| 200 mg/l | 5300 | 5100 | 5100 | 4900 | ○ |

The symbol X of the determination indicates that the MLSS value was not improved, the symbol Δ indicates that the MLSS value was slightly improved with respect to the blank sample, and the symbol ○ indicates that the improvement in the MLSS value was conspicuous.

For the sample with the amount of addition of the enzymatic treatment agent of 200 mg/l, the suspended sludge MLSS value decreased by about 4% with respect to the blank sample.

(Experimental Results)
Variation in phosphorus content (P) unit: mg/l

TABLE 27

| Amount of addition | Start | 24 hours | 48 hours | 72 hours | Determination |
|---|---|---|---|---|---|
| Blank | 0.8 | 0.8 | 0.8 | 0.8 | — |
| 100 mg/l | 0.8 | 0.7 | 0.7 | 0.7 | Δ |
| 200 mg/l | 0.8 | 0.7 | 0.6 | 0.7 | Δ |

The symbol X of the determination indicates that the sample exceeded the water quality regulation values, the symbol Δ indicates a sample in which the phosphorus content has decreased slightly with respect to the blank sample, and the symbol ○ indicates a sample in which the phosphorus content has been reduced.

The phosphorus content was reduced, though in a trace amount, in all the samples depending on the reaction time.

(Experiment Results)
Variation in T-N (nitrogen) content unit: mg/l

TABLE 28

| | Start | 24 hours | 48 hours | 72 hours | Determination |
|---|---|---|---|---|---|
| Blank | 16.4 | 17.6 | 19.4 | 24.8 | X |
| 100 mg/l | 16.4 | 16.4 | 13.3 | 14.7 | Δ |
| 200 mg/l | 16.4 | 16.1 | 12.8 | 11.3 | ○ |

The symbol X of the determination indicates a sample in which the T-N content exceeded the start blank value, the symbol Δ indicates a sample in which the T-N content increased slightly, and the symbol ○ indicates a sample in which the total amount of nitrogen decreased.

With regard to a sample that could maintain the start T-N value of the blank sample after 72 hours, the value decreased in both the 100 mg/l-added sample and the 200 mg/l-added sample; however, the effect of decrease in the 200 mg/l sample is high.

(Experiment Results)
Reaction of TOC/COD (TOC/COD) unit: mg/l

TABLE 29

| | Start | 24 hours | 48 hours | 72 hours | Determination |
|---|---|---|---|---|---|
| Blank | 28.7/14.0 | 25.4/8.5 | 24.6/4.4 | 23.7/6.4 | — |
| 100 mg/l | 28.7/14.0 | 22.7/7.7 | 22.4/4.3 | 22.6/5.8 | Δ |
| 200 mg/l | 28.7/14.0 | 21.5/6.7 | 20.2/4.3 | 18.9/4.7 | ○ |

The symbol Δ indicates that the value was improved, though to a very small extent, compared to the blank, and the symbol ○ indicates that the value decreased to a value lower than the blank value.

The 100 mg/l sample and the 200 mg/l sample, to which the enzymatic treatment agent was added, had both TOC and COD improved at the respective times with respect to the blank sample; however, results with a higher improvement effect were obtained with the 200 mg/l sample.

From the experiment results, as a countermeasure against deterioration of the water quality due to a nitrification reaction of the total nitrogen (T-N) caused by load variation of the raw water as the effect of adding the enzymatic treatment agent, the water quality reference values of 14.7 mg/l for the sample added with 100 mg/l of the enzymatic treatment agent and 11.3 mg/l for the sample added with 200 mg/l of the enzymatic treatment agent could be achieved, with respect to the blank value after 72 hours of 24.8 mg/l. Furthermore, by achieving suppression of nitrification, the water quality TOC value was improved by 20%, and the COD value was improved by 26% as a synergistic effect, and the MLSS value was improved by 4%.

Experiment of mixed water treatment agent using mixed liquid of green rust and enzymatic treatment agent A mixed water treatment agent of a green rust suspension and an enzymatic treatment agent for a food production effluent were added. Regarding the sample, a sample that was not subjected to addition (blank) and two units of continuous water passage apparatuses (capacity 5000 ml) were used to perform the experiment.

Regarding the mixed water treatment agent used, a mixed liquid of a green rust suspension and an enzymatic treatment agent at a mixing ratio of 90%:10% was adjusted with sodium hydroxide to a pH value of 7.0 and used.

The raw water was collected from a raw water adjustment tank for a food production effluent, was introduced into a supply tank (capacity 20 L), was transported to an aeration tank (capacity 5000 ml) with a quantitative pump and reacted, was subsequently passed through settling baffles (obstruction walls), and was precipitated. The supernatant water was measured as the treated water, and then the precipitated sludge was transported as return sludge to the inlet port of the aeration tank using a quantitative pump.

For the stirring of the aeration tank, an aeration pump (0.8 L/min) was used.

Regarding the activated sludge sample, an aeration tank sludge mixed liquid from a wastewater treatment plant of a food processing factory was collected and used. The properties of the collected water were as follows.

(Properties of Activated Sludge)

TABLE 30

| pH | MLSS (mg/l) | MLVSS (mg/l) | SV30 (%) |
|---|---|---|---|
| 7.9 | 5000 | 4400 | 99 |

MLSS: Sewage testing method Chapter 3 Section 6
MLVSS: Sewage testing method Chapter 3 Section 7
(Supernatant Separated Water)

TABLE 31

| Iron (mg/l) | Phosphorus (mg/l) | TOC (mg/l) | COD (mg/l) | T-N (mg/l) |
|---|---|---|---|---|
| 2.1 | 0.8 | 28.7 | 14 | 19.7 |

The following comparison experiment was performed using the present sample.
(Raw Water Adjustment Tank Collected Sample)

TABLE 32

| NO | pH | TOC (mg/l) | COD (mg/l) | T-N (mg/l) | T-P (mg/l) | Period of usage |
|---|---|---|---|---|---|---|
| A | 7.9 | 1440 | 1260 | 51 | 6.3 | 1 to 4 (days) |
| B | 7.1 | 1046 | 980 | 64 | 7.2 | 5 to 9 (days) |
| C | 7.3 | 1270 | 1310 | 76 | 5.1 | 10 to 14 (days) |

Raw Water Average Water Quality

TABLE 33

| TOC (mg/l) | COD (mg/l) | T-N (mg/l) | T-P (mg/l) |
|---|---|---|---|
| 1238 | 1177 | 64.5 | 6.2 |

The collected aerated liquid was tempered and aerated for 24 hours before starting the experiment, and a continuous water passage experiment was performed.
(Water Passage Load)
Amount of raw water passage=5000 ml/24 hours

TABLE 34

| Raw water load (A) | 1440 mg/l × 0.005 m$^3$ × 10$^{-3}$ = 0.0072 kg = 7.2 g/day |
|---|---|
| Raw water load (B) | 1046 mg/l × 0.005 m3 × 10−3 = 0.0052 kg = 5.2 g/day |
| Raw water load (C) | 1270 mg/l × 0.005 m3 × 10−3 = 0.0063 kg = 6.3 g/day |

(Experiment Results)
Regarding the addition of the mixed water treatment agent, addition is carried out with a quantitative pump installed in the aeration tank, with ON/OFF control and an ORP value of +30 mV.

TABLE 35

| | Blank | | | Mixed water treatment agent | | |
|---|---|---|---|---|---|---|
| Date (day) | pH | Do (mg/l) | ORP (mv) | pH | Do (mg/l) | ORP (mv) |
| Start | 7.6 | 0.87 | 34.1 | 7.6 | 0.67 | 27.6 |
| After 1 day | 7.5 | 1.1 | 36.4 | 7.6 | 0.97 | 18.3 |
| After 2 days | 7.3 | 0.72 | 33.4 | 7.7 | 0.98 | 14.2 |
| After 3 days | 7.2 | 0.62 | 34.8 | 7.7 | 1.1 | 19.7 |
| After 4 days | 7.4 | 0.98 | 41.2 | 7.8 | 1.2 | 26.7 |
| After 5 days | 7.5 | 1.2 | 57.6 | 7.7 | 1.4 | 28.4 |
| After 6 days | 7.6 | 1.4 | 66.8 | 7.8 | 1.5 | 27.3 |
| After 7 days | 7.7 | 1.6 | 74.6 | 7.8 | 1.4 | 23.6 |
| After 8 days | 7.6 | 1.7 | 76.8 | 7.7 | 1.4 | 21.3 |
| After 9 days | 7.7 | 1.8 | 81.7 | 7.8 | 1.2 | 23.4 |
| After 10 days | 7.8 | 1.9 | 74.6 | 7.8 | 1.3 | 22.1 |
| After 11 days | 7.8 | 2.1 | 72.4 | 7.9 | 1.6 | 23.4 |
| After 12 days | 7.7 | 2.6 | 70.8 | 7.9 | 1.4 | 27.4 |
| After 13 days | 7.6 | 1.9 | 72.4 | 8 | 1.2 | 23.4 |
| After 14 days | 7.6 | 1.7 | 69.8 | 7.8 | 1.1 | 22.8 |

Figure 6:
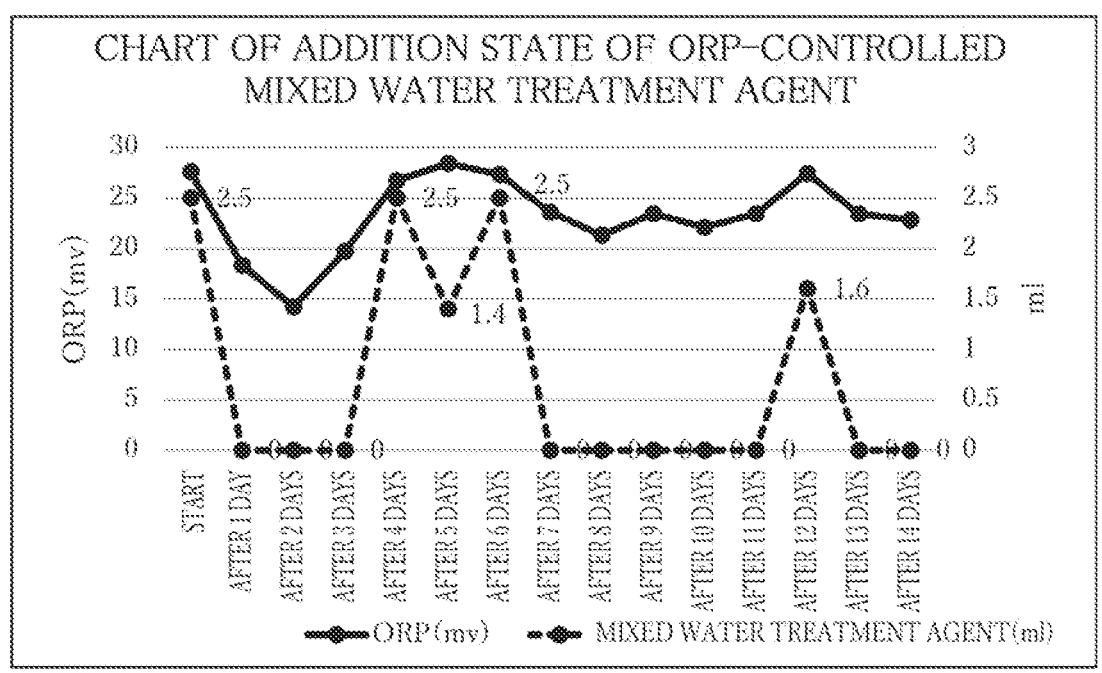
FIG. 6 is a chart of the addition state of an ORP-controlled mixed water treatment agent.
Figure 7:
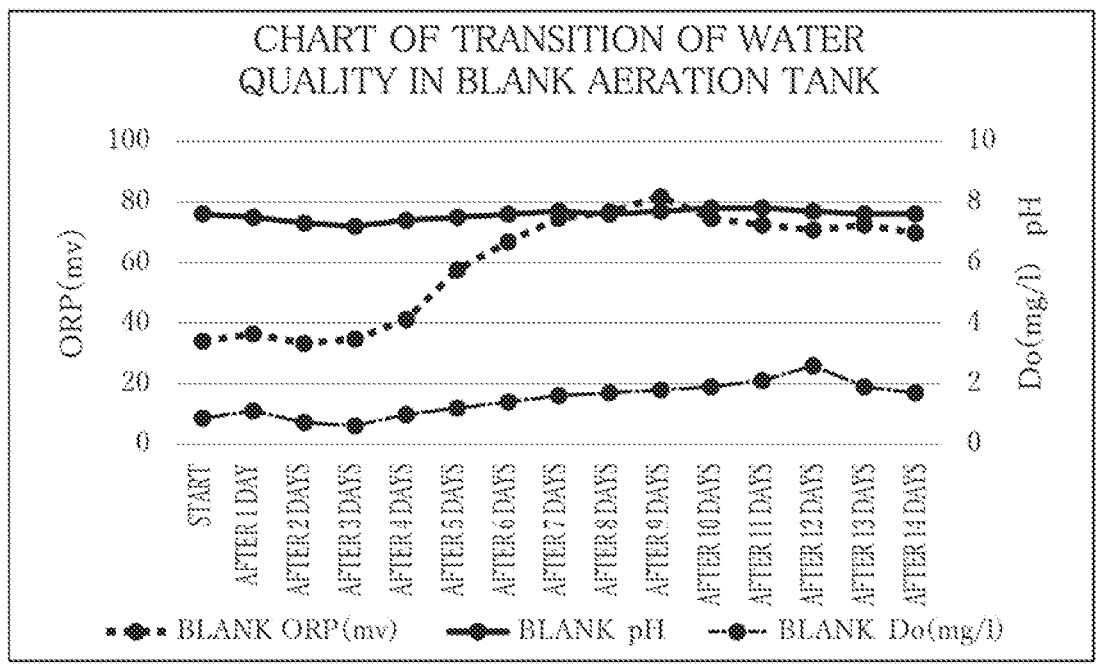
FIG. 7 is a chart of the transition of water quality in a blank aeration tank.
Figure 8:
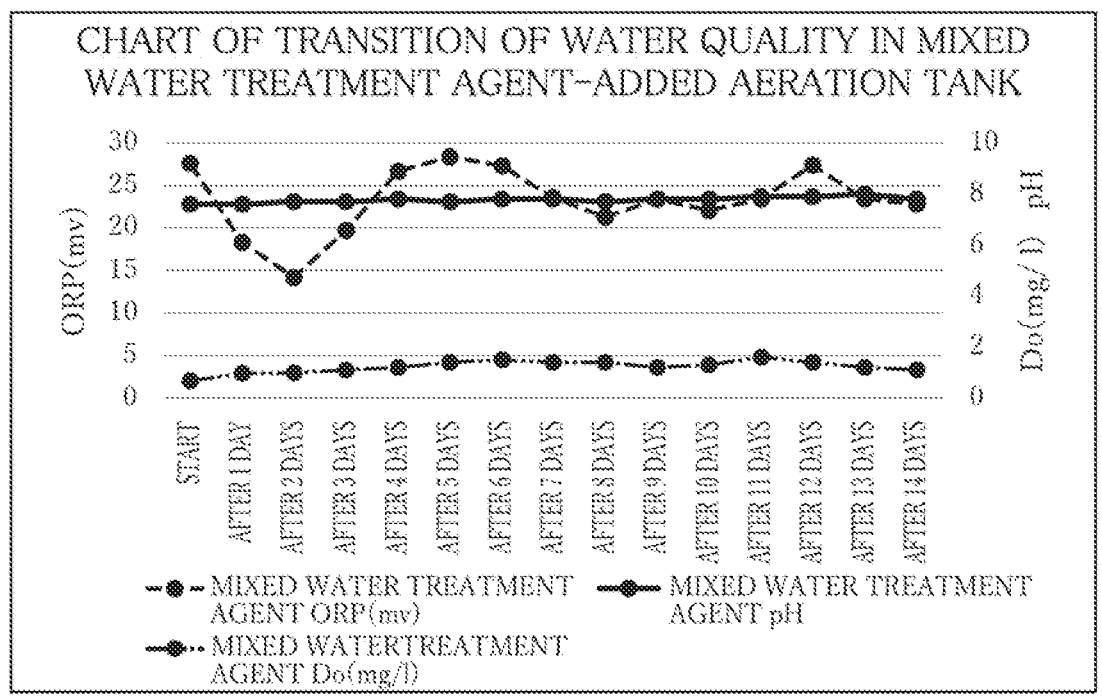
FIG. 8 is a chart of the transition of water quality in a mixed water treatment agent-added aeration tank.

On the 4th day, one unit of an aeration pump (0.8 L/min) for a blank aeration tank was added to one unit to provide two units in total.
Blank aeration quantity 1.6 L/min
(Amount of Addition of Mixed Water Treatment Agent)
Addition period: The amount reached 10.5 ml in 14 days, including 2.5 ml at the start.
The results are shown in FIGS. 6 to 8.

(Experiment Results)
Comparison of sludge concentration (MLSS) and sludge settling rate (5\730)

TABLE 36

| | Blank | | Mixed water treatment agent | |
|---|---|---|---|---|
| Item | MLSS (mg/l) | SV30 (%) | MLSS (mg/l) | SV30 (%) |
| Start | 5000 | 99 | 5000 | 99 |
| After 1 day | 4800 | 99 | 4900 | 99 |
| After 2 days | 4900 | 99 | 4800 | 98 |
| After 3 days | 5100 | 99 | 5000 | 97 |
| After 4 days | 5300 | 99 | 5100 | 94 |
| After 5 days | 5300 | 99 | 5100 | 95 |
| After 6 days | 5300 | 98 | 5100 | 92 |
| After 7 days | 5400 | 98 | 5000 | 88 |
| After 8 days | 5400 | 98 | 4900 | 82 |
| After 9 days | 5400 | 98 | 4900 | 79 |
| After 10 days | 5500 | 98 | 5000 | 76 |
| After 11 days | 5500 | 98 | 4800 | 71 |
| After 12 days | 5600 | 98 | 4800 | 68 |
| After 13 days | 5700 | 99 | 4700 | 61 |
| After 14 days | 5800 | 98 | 4700 | 56 |
| Determination | X | X | ○ | ○ |

The symbol ○ indicates that the values improved with respect to the blank.
Blank sample: The average MLSS and SV30 of the mixed water treatment agent sample were as follows.

TABLE 37

| Average value | Blank sample | Mixed water treatment agent-added sample |
|---|---|---|
| MLSS (mg/l) | 5333 | 4920 |
| SV30 (%) | 98.4 | 83.6 |

Figure 9:
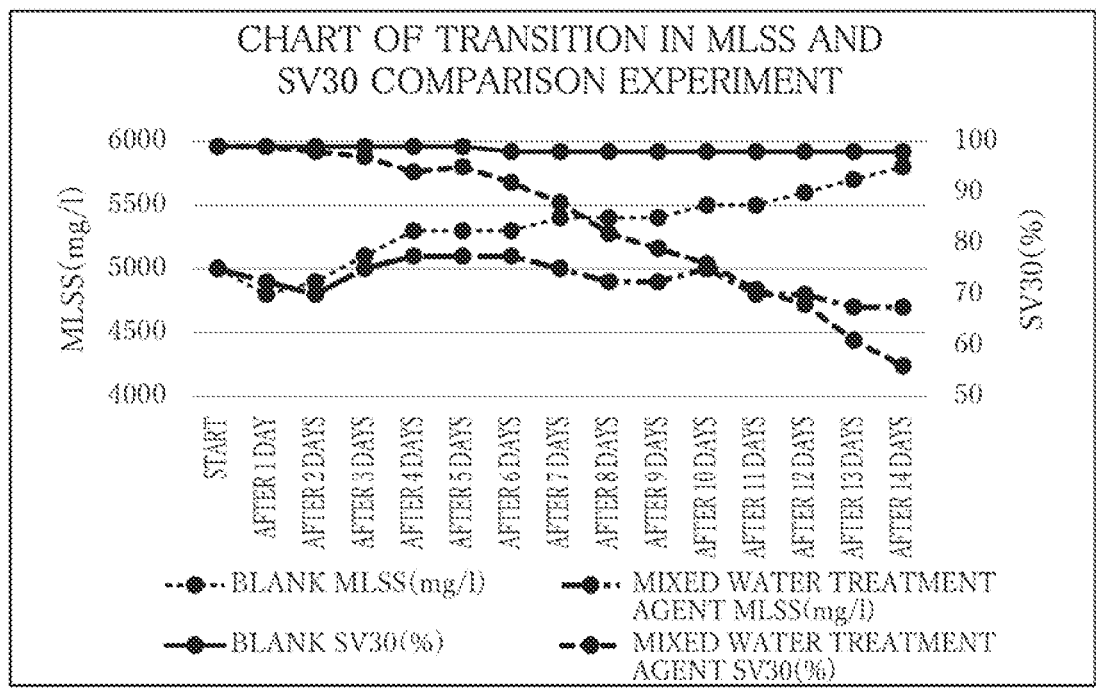
FIG. 9 is a chart of the transition in a MLSS and SV30 comparison experiment.

The results are shown in FIG. 9.
From the results of a comparison experiment for the MLSS and SV30, regarding the sludge settling rate (SV30), the sample added with the mixed suspension, as compared to the blank sample, was added with a mixed suspension recognized to have a tendency of improvement after the 4th to 5th day with respect to the blank sample, with ON/OFF control and an ORP value of +30 mV, and 10.5 ml was added in 14 days. Regarding the mixed liquor suspended solids (MLSS), both the blank and the mixed suspension sample exhibited an increase or a decrease after the 3$^{rd}$ day. Subsequently, the blank sample was considered to lack the stirring capacity, one unit of the aeration pump (0.8 L/min) was added on the 4th day to operate the system with two units, and thus the blank sample exhibited gentle increases after the 5th day.
(Experiment Results)
The respective samples for the MLSS-MLVSS values were subjected to a follow-up survey.

TABLE 38

| | Blank | | Mixed water treatment agent | |
|---|---|---|---|---|
| Item | MLSS (mg/l) | MLVSS (mg/l) | MLSS (mg/l) | MLVSS (mg/l) |
| Start | 5000 | 4400 | 5000 | 4400 |
| 5$^{th}$ day | 5300 | 4500 | 5100 | 4200 |
| 9$^{th}$ day | 5400 | 4400 | 4900 | 4200 |
| 14$^{th}$ day | 5800 | 4400 | 4700 | 4100 |
| Increment or decrement | 800 | ±0 | −300 | −300 |

(Experiment Results)

Comparison of organic carbon (TOC) and chemical oxygen demand (COD)

Place of water collection Supernatant water separated by settling

Raw water concentration (average value) TOC 1238 mg/l COD 1177 mg/l

TABLE 39

|  | Blank | | Mixed water treatment agent | |
|---|---|---|---|---|
| Item | TOC (mg/l) | COD (mg/l) | TOC (mg/l) | COD (mg/l) |
| Start | 96.4 | 74 | 96.4 | 74 |
| After 1 day | 64.2 | 48 | 43.7 | 28 |
| After 2 days | 49.8 | 42 | 25.4 | 20 |
| After 3 days | 44.3 | 39 | 22.7 | 17 |
| After 4 days | 41.5 | 34 | 19.7 | 15 |
| After 5 days | 38.4 | 30 | 17.5 | 12 |
| After 6 days | 31.4 | 28 | 14.6 | 9.4 |
| After 7 days | 29.4 | 20 | 14.4 | 8.5 |
| After 8 days | 25.9 | 17 | 12.4 | 8.6 |
| After 9 days | 27.6 | 18 | 12.6 | 9.7 |
| After 10 days | 28.8 | 21 | 12.8 | 10.4 |
| After 11 days | 28.4 | 21 | 11.2 | 9.4 |
| After 12 days | 22.1 | 19 | 12.2 | 11 |
| After 13 days | 21.8 | 18 | 11.4 | 10 |
| After 14 days | 23.8 | 18 | 10.6 | 8.6 |
| Determination | X | X | ○ | ○ |

The symbol ○ indicates an improvement with respect to the blank.

The average treated water quality for 14 days is shown.

TABLE 40

| Average value | Blank sample | Mixed water treatment agent-added sample |
|---|---|---|
| TOC (mg/l) | 38.2 | 22.5 |
| COD (mg/l) | 29.3 | 16.7 |

Figure 10:
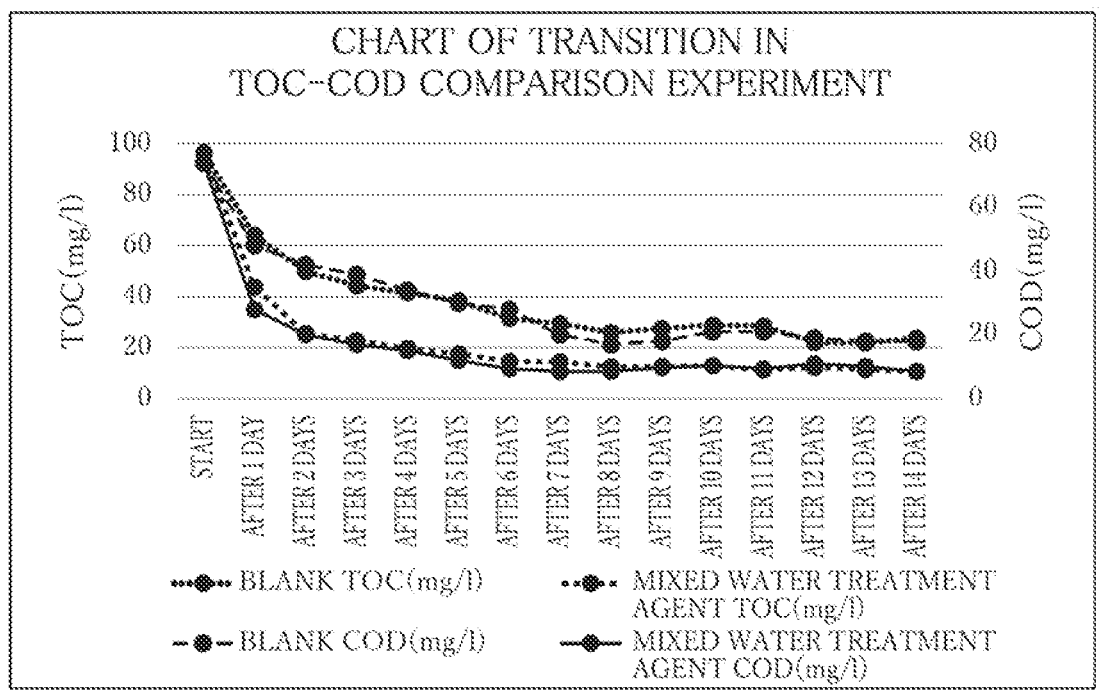
FIG. 10 is a chart of the transition in a TOC-COD comparison experiment.

The results are shown in FIG. 10.

(Experiment Results)

Comparison of total nitrogen (T-N) and total phosphorus (T-P)

Place of water collection Supernatant water separated by settling

Raw water concentration (average value) T-N 64.5 mg/l T-P 6.2 mg/l

TABLE 41

|  | Blank | | Mixed water treatment agent | |
|---|---|---|---|---|
| Item | T-N (mg/l) | T-P (mg/l) | T-N (mg/l) | T-P (mg/l) |
| Start | 21.4 | 4.2 | 21.4 | 4.2 |
| After 1 day | 27.3 | 3.6 | 19.7 | 0.8 |
| After 2 days | 26.7 | 3.3 | 11.5 | 0.4 |
| After 3 days | 27.4 | 2.8 | 10.2 | 0.3 |
| After 4 days | 28.6 | 2.5 | 10.5 | 0.4 |
| After 5 days | 26.4 | 2.4 | 12.4 | 0.4 |
| After 6 days | 24.8 | 2.2 | 10.6 | 0.3 |
| After 7 days | 27.3 | 2.3 | 9.4 | 0.3 |
| After 8 days | 26.4 | 2.1 | 8.7 | 0.4 |
| After 9 days | 25.7 | 2.4 | 9.2 | 0.3 |
| After 10 days | 24.2 | 2.2 | 11.3 | 0.4 |
| After 11 days | 25.8 | 2.3 | 10.3 | 0.3 |
| After 12 days | 30.2 | 2 | 10.8 | 0.4 |
| After 13 days | 31.4 | 1.9 | 9.7 | 0.4 |
| After 14 days | 29.8 | 1.3 | 10.2 | 0.3 |
| Determination | X | X | ○ | ○ |

The symbol ○ indicates an improvement with respect to the blank.

The average treated water quality for 14 days is shown.

TABLE 42

| Average value | Blank sample | Mixed water treatment agent-added sample |
|---|---|---|
| T-N (mg/l) | 26.8 | 11.7 |
| T-P (mg/l) | 2.5 | 0.64 |

Figure 11:
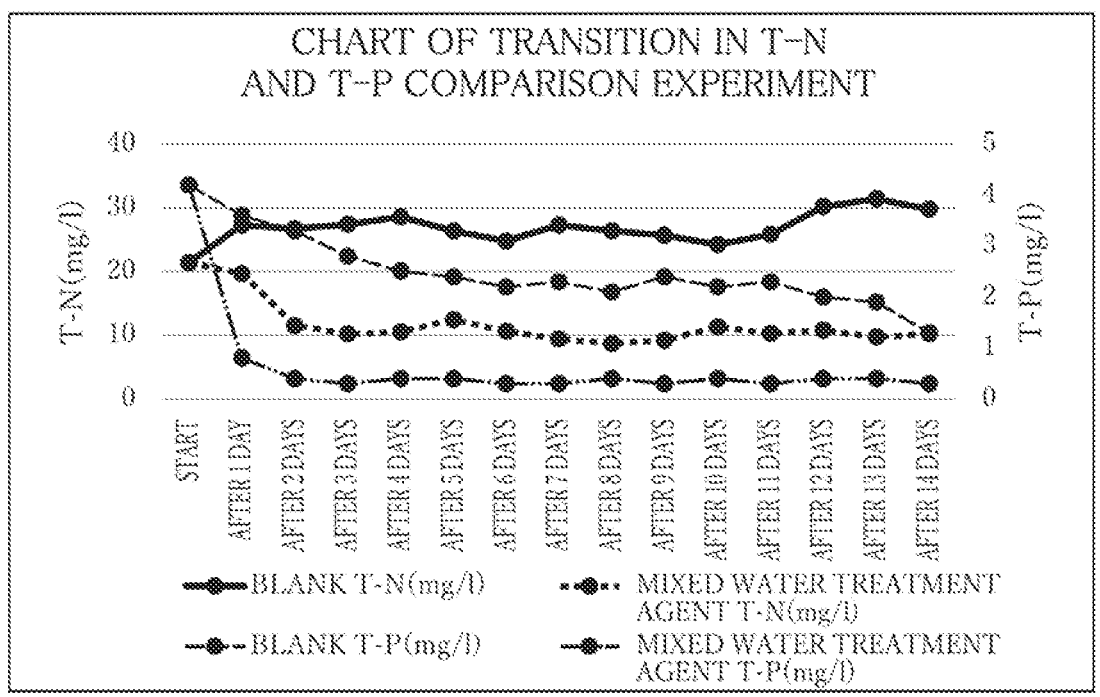
FIG. 11 is a chart of the transition in a T-N and T-P comparison experiment.

The results are shown in FIG. 11.

(Experiment Results)

Variation in the ammoniacal nitrogen (NH4-N) and nitrate nitrogen (NO3-N)

Place of water collection Supernatant water separated by settling

Measuring method Ion analysis apparatus

TABLE 43

|  | Blank sample | | | Mixed water treatment agent-added sample | | |
|---|---|---|---|---|---|---|
| Date | pH | NH4-N (mg/1) | NO3-N (mg/1) | pH | NH4-N (mg/1) | NO3-N (mg/1) |
| Before start | 7.6 | 52.4 | 4.42 | 7.6 | 52.4 | 4.42 |
| 4th day | 7.4 | 84.6 | 6.46 | 7.8 | 24.8 | 8.42 |
| 8th day | 7.6 | 28.6 | 54.7 | 7.8 | 21.6 | 12.4 |
| 14th day | 7.6 | 22.6 | 58.7 | 8 | 8.76 | 8.42 |

From the results of an ion analysis, regarding the blank sample, the cause for adding one unit of an aeration pump due to poor treated water quality on the 4th day was also included, and thereafter, the nitrate nitrogen increased so that the blank sample was in a nitrified state. Regarding the mixed water treatment agent-added sample, the ammoniacal nitrogen content of the organic nitrogen was decreased from the value before the start to the 14th day, and the nitrate nitrogen increased from the value before the start; however, the amount was a trace amount.

As a countermeasure to avoid a nitrification reaction of an aerated liquid, the avoidance could be achieved by adding the mixed water treatment agent.

The invention claimed is:

1. A water treatment agent comprising:
    green rust; and
    an enzymatic treatment agent containing a liver extract from a mammal (excluding a human being), a yeast lytic enzyme, lactate dehydrogenase, a glucose dehydrogenase, and water.

2. A method for producing a water treatment agent, the method comprising
    obtaining the water treatment agent according to claim 1 by mixing:
    green rust; and
    an enzymatic treatment agent containing a liver extract from a mammal (excluding a human being), a yeast lytic enzyme, lactate dehydrogenase, a glucose dehydrogenase, and water.

3. A method for treating water to be treated, the method comprising bringing a water to be treated including nitrogen-containing compounds, into contact with the water treatment agent according to claim 1.

4. The method for treating water to be treated according to claim 3, wherein the nitrogen-containing compounds include nitrate nitrogen.

5. The method for treating water to be treated according to claim 3, wherein the water to be treated is an effluent from a food factory.

6. A kit for producing the water treatment agent according to claim 1, the kit comprising:
- a first container accommodating a green rust suspension;
- a second container accommodating an enzymatic treatment agent containing a liver extract from a mammal (excluding a human being), a yeast lytic enzyme, lactate dehydrogenase, a glucose dehydrogenase, and water; and
- a manual describing a method for producing the water treatment agent according to claim 1 from the green rust suspension and the enzymatic treatment agent.

7. The method for treating water to be treated according to claim 4, wherein the water to be treated is an effluent from a food factory.

* * * * *